US010449200B2

(12) United States Patent
Yen et al.

(10) Patent No.: US 10,449,200 B2
(45) Date of Patent: Oct. 22, 2019

(54) COMBINED INHIBITION OF THE VITAMIN D RECEPTOR AND POLY(ADP) RIBOSE POLYMERASE (PARP) IN THE TREATMENT OF CANCER

(71) Applicant: Institute for Cancer Research, Philadelphia, PA (US)

(72) Inventors: Timothy J. Yen, Haverford, PA (US); Vikram Bhattacharjee, Philadelphia, PA (US)

(73) Assignee: The Research Institute of Fox Chase Cancer Center, Philadelphia, PA (US)

( * ) Notice: Subject to any disclaimer, the term of this patent is extended or adjusted under 35 U.S.C. 154(b) by 0 days.

(21) Appl. No.: 15/848,537

(22) Filed: Dec. 20, 2017

(65) Prior Publication Data
US 2018/0221381 A1 Aug. 9, 2018

Related U.S. Application Data

(63) Continuation of application No. 14/882,553, filed on Oct. 14, 2015, now Pat. No. 9,889,141.
(60) Provisional application No. 62/063,581, filed on Oct. 14, 2014.

(51) Int. Cl.
| A61K 31/55 | (2006.01) |
| A61K 31/7068 | (2006.01) |
| A61K 45/06 | (2006.01) |
| A61K 31/593 | (2006.01) |

(52) U.S. Cl.
CPC ............ *A61K 31/55* (2013.01); *A61K 31/593* (2013.01); *A61K 31/7068* (2013.01); *A61K 45/06* (2013.01)

(58) Field of Classification Search
None
See application file for complete search history.

(56) References Cited

U.S. PATENT DOCUMENTS

| 2003/0125271 A1 | 7/2003 | Baker et al. |
| 2005/0182033 A1 | 8/2005 | DeLuca et al. |
| 2005/0272688 A1 | 12/2005 | Higgins et al. |
| 2008/0293647 A1 | 11/2008 | Adorini et al. |
| 2009/0076091 A1 | 3/2009 | Klein et al. |
| 2009/0149377 A1 | 6/2009 | Takagi et al. |
| 2011/0178163 A1 | 7/2011 | Chowdhury |

FOREIGN PATENT DOCUMENTS

WO 2005012524 2/2005

OTHER PUBLICATIONS

Chiang et al., "Vitamin D for the prevention and treatment of pancreatic cancer", Word J. Gastroenterol, 2009, 15(27): 3349-3354.

Adorini, L. et al., "Vitamin D receptor agonists, cancer and the immune system: an intricate relationship", Curr. Top Med Chem, 2006, 6(12):1297-1301.
Beer, T.M. et al., "Double-Blinded Randomized Study of High-Dose Calcitrol Plus Docetaxel Compared With Placebo Plus Doxetaxel in Androgen-Independent Prostate Cancer: A Report From the ASCENT Investigators", J. Clin. Oncol., 2007, 25(6):669-674.
Bouffard et al., "Kinetic studies on 2', 2'-difluorodeoxycytidine (Gemcitabine) with purified human deoxycytidine kinase and cytidine deaminase", Biochem. Pharmacol., 1993, 45(9):1857-1861 (abstract only).
Deeb, K.K. et al., "Vitamin D signaling pathways in cancer: potential for anticancer therapeutics", Nat. Rev. Cancer, 2007,7(9):684-700.
Getzenberg, R.H. et al., "Vitamin D inhibition of prostate adenocarcinoma growth and metastasis in the Dunning rat prostate model system", Urology, 1997, 50(6):999-1006.
Herschberger, P.A. et al., "Calcitrol (1,25-Dihydroxycholecalciferol) Enhances Paclitaxel Antitumor Activity in Vitro and in Vivo and Accelerates Paclitaxel-induced Apoptosis", Clin. Cancer Res., 2001, 7:1043-1051.
International Search Report and Written Opinion issued in PCT/US2012/039242 dated Aug. 1, 2012.
Krishnan, A.V. et al., "Calcitriol as a chemopreventative and therapeutic agent in prostate cancer: role of anti-inflammatory activity", J. Bone Miner Res., 2007, 22 Suppl 2:V74-80.
McElwain, M.C. et al., "Vitamin D: an antiproliferative agent with potential for therapy of squamous cell carcinoma", Am. J. Otolaryngol, 1997, 18(5):293-298.
Moffatt, K.A. et al., "1a, 25-Dihydroxyvitamin D3 and Platinum Drugs Act Synergistically to Inhibit the Growth of Prostate Cancer Cell Lines", Clin. Cancer Res., 1999, 5:695-703.
Moore, M.J. "Brief communication: a new combination in the treatment of advanced pancreatic cancer", Semin. Oncol., 2005, 32(6 Suppl.)5-6.
Nigro, J.M. et al., "Mutations in the p53 gene occur in diverse human tumour types", Nature, 1989, 343(6250)705-708.
Ordonez-Moran, P. et al., "Vitamin D and cancer: an update of in vitro and in vivo date", Front Biosci., 2005, 10:2723-2749.
Philip, P. et al.,"Consensus Report of the National Cancer Institute Clinical Trials Planning Meeting on Pancreas Cancer Treatment", J. Clin. Oncol., 2009, 27(33):5660-5669.
Saito, N. et al., "Highly potent vitamin D receptor antagonists: design, synthesis, and biological evaluation", Chembiochem, 2006, 7(10):1479-1490.
Trump, D.L et al., "Phase II Trial of High-Dose, Intermittent Calcitrol (1, 25 Dihodroxyvitamin D3) and Dexamethasone in Androgen-Independent Prostate Cancer", Cancer, 2006, 106(10):2136-2142.
Van Cutsem, E et al., "Phase III Trial of Gemcitabine Plus Tipifarnib Compared with Gemcitabine Plus Placebo in Advanced Pancreatic Cancer", J. Clin. Oncol., 2004, 22(8):1430-1438.

(Continued)

*Primary Examiner* — Ekaterina Poliakova-Georgantas
(74) *Attorney, Agent, or Firm* — Stradley Ronon Stevens & Young, LLP

(57) ABSTRACT

Methods for treating tumors comprise contacting tumor cells expressing the vitamin D receptor with a vitamin D receptor ligand that inhibits homologous recombination in the tumor cells, and contacting the tumor cells with an amount of a Poly(ADP) Ribose Polymerase 1 (PARP-1) inhibitor. Inhibiting homologous recombination produces a synergistic therapeutic effect between the vitamin D receptor ligand and PARP-1 inhibitor, and may overcome PARP-1 resistance in killing tumor cells.

20 Claims, 26 Drawing Sheets

Specification includes a Sequence Listing.

(56) References Cited

OTHER PUBLICATIONS

Van den Bemd, G.J. et al., "Vitamin D and vitamin D analogs in cancer treatment", Curr. Drug Targets, 2002, 3(1):85-94.

Ylikomi, et al., "Antiproliferative Action of Vitamin D", Vitamins and Hormones, 2002, 64:357-406.

Zhang, X. et al., "Growth Suppression of Ovarian Cancer Xenografts in Nude Mice by Vitamin D Analogue EB 1089", Clin. Cancer Res., 2005, 11:323-328.

Mabley et al., "Inhibition of poly(adenosine diphosphate-ribonse) polymerase by the active form of vitamin D", International Journal of Molecular Medicine, 2007, International Journal of Molecular Medicine, 19:947-952.

Awashi et al., "Evaluation of Poly-Mechanistic Antiangiogenic Combinations to Enhance Cytotoxix Therapy Response in Pancreatic Cancer", Plos One, 2012, 7(6) 338477: 1-12.

Porcelli et al., "Optimize radiochemotherapy in pancreatic cancer: PARP inhibitors a new therapeutic opportunity", Molecular Oncology, 2013, 7:308-322.

Chiang et al., "Vitamin D for the prevention and treatment of pancreatic cancer", World J Gastroenterol, 2009, 15(27):3349-3354.

A

B

E

F

A

SEQUENCE LISTING

```
<160> NUMBER OF SEQ ID NOS: 16

<210> SEQ ID NO 1
<211> LENGTH: 18
<212> TYPE: RNA
<213> ORGANISM: Homo sapiens

<400> SEQUENCE: 1
caaccaagac uacaagua                                                 18

<210> SEQ ID NO 2
<211> LENGTH: 57
<212> TYPE: RNA
<213> ORGANISM: Homo sapiens

<400> SEQUENCE: 2
ccggccucca guucguguga augaucucga gaucauucac acgaacugga gguuuuu      57

<210> SEQ ID NO 3
<211> LENGTH: 57
```

```
<212> TYPE: RNA
<213> ORGANISM: Homo sapiens

<400> SEQUENCE: 3
ccggcgaagu guuggcaau gagaucucga gaucucauug ccaaacacuu cguuuuu        57

<210> SEQ ID NO 4
<211> LENGTH: 19
<212> TYPE: RNA
<213> ORGANISM: Homo sapiens

<400> SEQUENCE: 4
gcgcaucauu gccauacug                                                 19

<210> SEQ ID NO 5
<211> LENGTH: 19
<212> TYPE: RNA
<213> ORGANISM: Homo sapiens

<400> SEQUENCE: 5
ccaacacacu gcagacgua                                                 19

<210> SEQ ID NO 6
<211> LENGTH: 19
<212> TYPE: RNA
<213> ORGANISM: Homo sapiens

<400> SEQUENCE: 6
gcaaugagau cuccugacu                                                 19

<210> SEQ ID NO 7
<211> LENGTH: 21
<212> TYPE: RNA
<213> ORGANISM: Homo sapiens

<400> SEQUENCE: 7
cgaaguguuu ggcaaugaga u                                              21

<210> SEQ ID NO 8
<211> LENGTH: 19
<212> TYPE: RNA
<213> ORGANISM: Homo sapiens

<400> SEQUENCE: 8
gcaacaguau uucgguaua                                                 19

<210> SEQ ID NO 9
<211> LENGTH: 19
<212> TYPE: RNA
<213> ORGANISM: Homo sapiens

<400> SEQUENCE: 9
ggacuucucu ccaguaaac                                                 19

<210> SEQ ID NO 10
<211> LENGTH: 19
<212> TYPE: RNA
<213> ORGANISM: Homo sapiens

<400> SEQUENCE: 10
aaagauagau gguacaaca                                                 19

<210> SEQ ID NO 11
```

```
<211> LENGTH: 19
<212> TYPE: RNA
<213> ORGANISM: Homo sapiens

<400> SEQUENCE: 11
agauaugaag cgugccgua                                               19

<210> SEQ ID NO 12
<211> LENGTH: 19
<212> TYPE: RNA
<213> ORGANISM: Homo sapiens

<400> SEQUENCE: 12
gagagcagau gauccuuua                                               19

<210> SEQ ID NO 13
<211> LENGTH: 19
<212> TYPE: RNA
<213> ORGANISM: Homo sapiens

<400> SEQUENCE: 13
ggacaagucu cucagcuau                                               19

<210> SEQ ID NO 14
<211> LENGTH: 19
<212> TYPE: RNA
<213> ORGANISM: Homo sapiens

<400> SEQUENCE: 14
gauaucagcu uagacaauu                                               19

<210> SEQ ID NO 15
<211> LENGTH: 19
<212> TYPE: RNA
<213> ORGANISM: Homo sapiens

<400> SEQUENCE: 15
ggacagaacc cgcagauuu                                               19

<210> SEQ ID NO 16
<211> LENGTH: 21
<212> TYPE: RNA
<213> ORGANISM: Homo sapiens

<400> SEQUENCE: 16
gcuaccuauc acagagcaau u                                            21
```

COMBINED INHIBITION OF THE VITAMIN D RECEPTOR AND POLY(ADP) RIBOSE POLYMERASE (PARP) IN THE TREATMENT OF CANCER

CROSS REFERENCE TO RELATED APPLICATIONS

This application is a continuation of U.S. Ser. No. 14/882,553, filed on Oct. 14, 2015, now U.S. Pat. No. 9,889,141, issued on Feb. 13, 2018, which claims priority to U.S. provisional application No. 62/063,581, filed on Oct. 14, 2014, the contents of which are incorporated by reference herein, in their entirety and for all purposes.

REFERENCE TO GOVERNMENT GRANTS

This invention was made with government support under Grant No. CA169706 and Grant No. CA182651 awarded by The National Institutes of Health. The government has certain rights in the invention.

REFERENCE TO A SEQUENCE LISTING

This application includes a Sequence Listing submitted electronically as a text file named VDR+PARP_ST25.txt, created on Oct. 9, 2015, with a size of 3000 bytes. The Sequence Listing is incorporated by reference herein.

FIELD OF THE INVENTION

The invention relates generally to the field of cancer treatment. More particularly, the invention relates to combination therapies for treating cancer cells expressing the vitamin D receptor, especially pancreatic cancer cells, by inhibiting homologous recombination in such cells, thereby enhancing the susceptibility of the cells to inhibitors of poly(ADP)-ribose polymerase (PARP).

BACKGROUND OF THE INVENTION

Various publications, including patents, published applications, technical articles and scholarly articles are cited throughout the specification. Each of these cited publications is incorporated by reference herein, in its entirety and for all purposes.

Pancreatic cancer (PCa) is the 4th leading cause of cancer fatality in the United States and has the lowest 5-year survival rate of any major cancer (ACS). More than 70% of patients die within the first year after being diagnosed. By year 2020, it is anticipated that PCa will move to the 2nd leading cause of cancer death. At the time of diagnosis, over 52% of the patients have distant disease and 26% have regional spread. Only ~15% of patients diagnosed with pancreatic adenocarcinoma can have their tumors surgically removed. Lack of early diagnosis, complex biology of the disease, and limited treatment options contribute to making PCa a major killer.

Virtually all pancreatic tumors are adenocarcinomas of which the vast majority expresses a mutant K-Ras. Over two decades of PCa research suggest a model for disease progression where early, low-grade pancreatic intraepithelial neoplasia (PanIN), is associated with KRAS2 mutations and telomere shortening. Intermediate and late stages of the disease are characterized by loss of p16/CDKN2A, SMAD4, p53, and BRCA2 respectively. Additionally, a massive effort to sequence the genomes of 24 independently derived advanced pancreatic adenocarcinomas revealed a remarkably complex pattern of genetic mutations. On average, there were 63 genetic mutations in PCa. The majority (67%) of the mutations could be classified into 12 partially overlapping cellular signaling pathways.

PCas are notoriously insensitive to the backbone of cancer chemo- and radiation therapy, all of which target processes essential for the integrity of the genome. Understanding the mechanisms of chemoresistance of PCa will provide new targets that enhance cell killing.

SUMMARY OF THE INVENTION

The disclosure features combination therapies for treating cancer cells expressing the vitamin D receptor (VDR), and especially its use for enhancing the susceptibility of cancer cells to Poly(ADP) Ribose Polymerase 1 (PARP-1) inhibition, for example, by inactivating this receptor in order to inhibit homologous recombination in the cells. It is believed that the efficacy of PARP inhibition hinges, at least in part, on impaired or a lack of homologous recombination.

In some aspects, the therapeutic methods comprise killing tumor cells expressing the vitamin D receptor by contacting the vitamin D receptor on the tumor cells with a vitamin D receptor ligand, and contacting the tumor cells with an amount of a Poly(ADP) Ribose Polymerase 1 (PARP-1) inhibitor. The combination of the vitamin D receptor ligand and PARP-1 inhibitor exhibits therapeutic synergy in killing the tumor cells. The ligand may inactivate vitamin D receptor-mediated homologous recombination. The tumor cells may be resistant to the PARP-1 inhibitor. The tumor cells may be pancreatic tumor cells, lung tumor cells, breast tumor cells, ovarian tumor cells, lymph node tumor cells, bladder tumor cells, prostate tumor cells, or esophageal tumor cells. Pancreatic tumor cells are preferred. The method is preferably carried out in vivo, and more preferably in a human subject.

The vitamin D receptor ligand may be an agonist or antagonist of the vitamin D receptor, or may competitively inhibit a second ligand that is expressed by the tumor, with this second ligand having some activity that induces, enhances, facilitates, potentiates, or otherwise causes vitamin D Receptor activity that protects the tumor, for example, via homologous recombination and DNA repair. The ligand may be used in an amount effective to inhibit homologous recombination in the tumor cells. The ligand may be a vitamin D analog. The vitamin D receptor ligand may be an antagonist of the vitamin D receptor. The ligand may comprise calcitriol, calcipotriol, eldecalcitol, lisinopril, elocalcitol, paricalcitol, seocalcitol, or any combination thereof. The ligand may comprise TEI-9647, TEI-9648, OU-72 (U.S. Publ, No. 2005/0182033), or a derivative or analog thereof. The PARP-1 inhibitor may comprise olaparib, iniparib, rucaparib, veliparib, MK 4827, BMN673, BSI 401, or any combination thereof.

Alternatively to contacting the vitamin D receptor with a ligand, the method may comprise inhibiting the expression of the vitamin D receptor, for example, by transforming the tumor cells with a nucleic acid molecule that inhibits the expression of the vitamin D receptor in the tumor cells. The combination of inhibiting the expression of the vitamin D receptor and PARP-1 inhibition exhibits therapeutic synergy in killing the tumor cells.

The method may further comprise inducing double stranded DNA breaks in the chromosomal DNA of the tumor cells. Inducing double stranded DNA breaks may comprise irradiating the chromosomal DNA of the tumor cells. Inducing double stranded DNA breaks may comprise contacting the tumor cells with an amount of gemcitabine effective to induce double stranded DNA breaks.

In some detailed aspects, the method comprises contacting the vitamin D receptor of the pancreatic tumor cells with a vitamin D receptor ligand, and then contacting the pancreatic tumor cells with an amount of the PARP-1 inhibitor. The combination the vitamin D receptor ligand and PARP-1 inhibitor exhibits therapeutic synergy in killing the pancreatic tumor cells. The pancreatic tumor cells may be resistant to the PARP-1 inhibitor. The vitamin D receptor ligand may be an agonist or antagonist of the vitamin D receptor, or may competitively inhibit a second ligand that is expressed by the tumor, with this second ligand having some activity that induces, enhances, facilitates, potentiates, or otherwise causes vitamin D Receptor activity that protects the tumor, for example, via homologous recombination and DNA repair. The ligand may be used in an amount effective to inhibit homologous recombination in the tumor cells. The ligand may be a vitamin D analog. The vitamin D receptor ligand may be an antagonist of the vitamin D receptor. The ligand may comprise calcitriol, calcipotriol, eldecalcitol, lisinopril, elocalcitol, paricalcitol, seocalcitol, or any combination thereof. The ligand may comprise TEI-9647, TEI-9648, OU-72, or a derivative or analog thereof. The PARP-1 inhibitor may comprise olaparib, iniparib, rucaparib, veliparib, MK 4827, BMN673, BSI 401, or any combination thereof. The method may further comprise inducing double stranded DNA breaks in the chromosomal DNA of the tumor cells. Inducing double stranded DNA breaks may comprise irradiating the chromosomal DNA of the tumor cells. Inducing double stranded DNA breaks may comprise contacting the tumor cells with an amount of gemcitabine effective to induce double stranded DNA breaks.

In some aspects, the therapeutic methods comprise killing tumor cells by inhibiting Rad51 in the tumor cells sufficiently to inhibit homologous recombination in the tumor cells, and contacting the tumor cells with an amount of a Poly(ADP) Ribose Polymerase 1 (PARP-1) inhibitor. The combination of Rad51 inhibition and PARP-1 inhibition exhibits therapeutic synergy in killing the tumor cells. The tumor cells may be resistant to the PARP-1 inhibitor. The tumor cells may be pancreatic tumor cells, lung tumor cells, breast tumor cells, ovarian tumor cells, lymph node tumor cells, bladder tumor cells, prostate tumor cells, or esophageal tumor cells. Pancreatic tumor cells are preferred. The method is preferably carried out in vivo, and more preferably in a human subject.

DETAILED DESCRIPTION OF THE INVENTION

Figure 1:
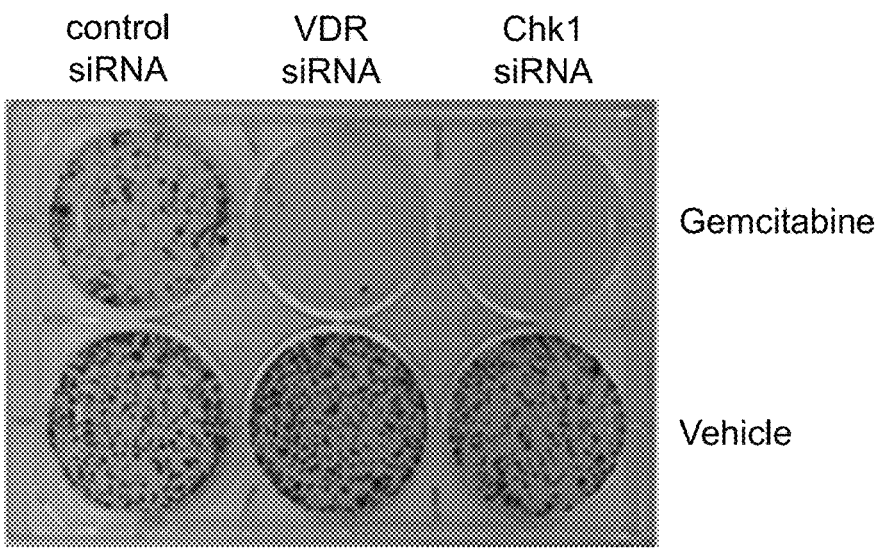
FIG. 1: Sensitization of pancreatic cancer cells to gemcitabine following VDR knockdown. (A) Colony formation assay comparing gemcitabine sensitivity of Panc1 cells after control, VDR and Chk1 siRNA transfection. Cells were treated with 50 nM gemcitabine for 24 hrs. and drug removed before the assay. Colony counts are presented beneath the image of a representative colony survival assay. (B) Gemcitabine kill curves from clonogenic survival assays performed on BXPC3, Panc1 and CFPAC1 cells following control or VDR siRNA transfection (n=5). p values: BxPC3=0.036, Panc1=0.171, CFPAC1=0.083. (C) clonogenic survival assays of gemcitabine sensitivity of BxPC3 VDRkd cells transfected with the indicated VDR constructs (n=5). p values: VDR-WT=0.088, VDR-C288G=0.671, VDR-K246G=0.845, VDR-L254G=0.148. (D) AML1/ETO and VDR-5237M neutralizes the ability of WT-VDR to rescue gemcitabine resistance of BxPC3 VDRkd cells (n=5). p values: AML1/ETO=0.147, VDR-5237M=0.039. (E) Western blot showing VDR expression after 18 hour vehicle or gemcitabine (50 nM) treatment of PCa cell lines. 40 μg of protein loaded. Lane 1=Panc1+Vehicle; Lane 2=Panc1+gemcitabine; Lane 3=CFPAC1+Vehicle; Lane 4=CFPAC1+gemcitabine; Lane 5=BxPC3+Vehicle; Lane 6=BxPC3+gemcitabine. The 55 kDa marker is labeled between lanes 2 and 3, and to the right of lane 6. (F) Increased resistance of Panc1 cells to gemcitabine following VDR 898 overexpression (n=5). p value=0.008.
Figure 1:
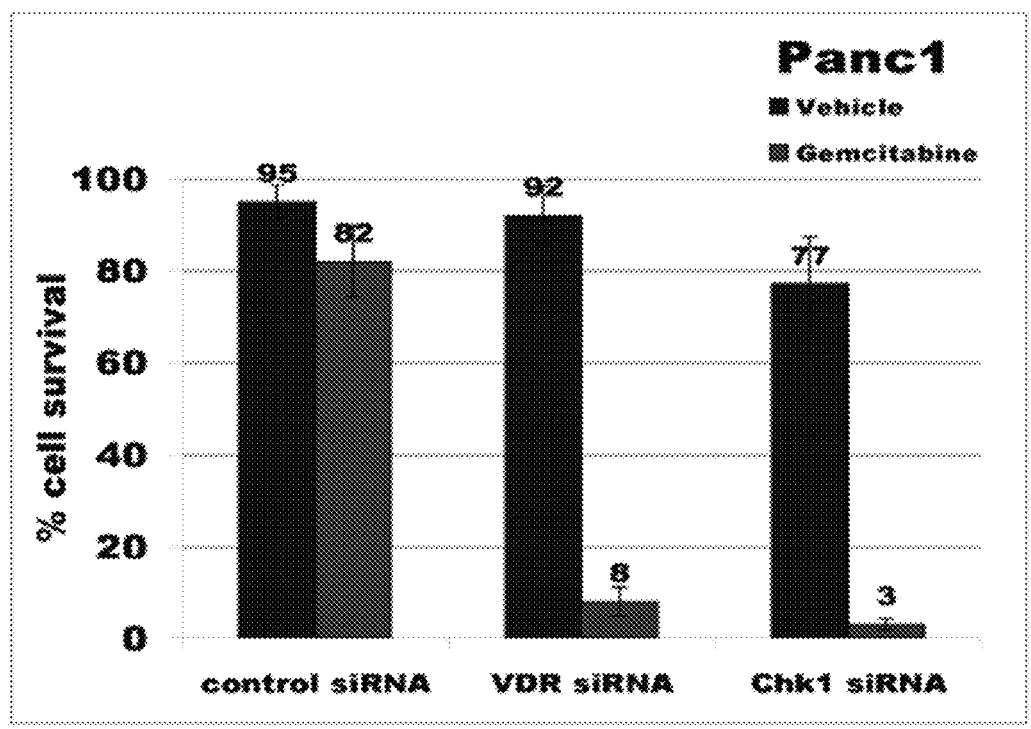
Figure 1:
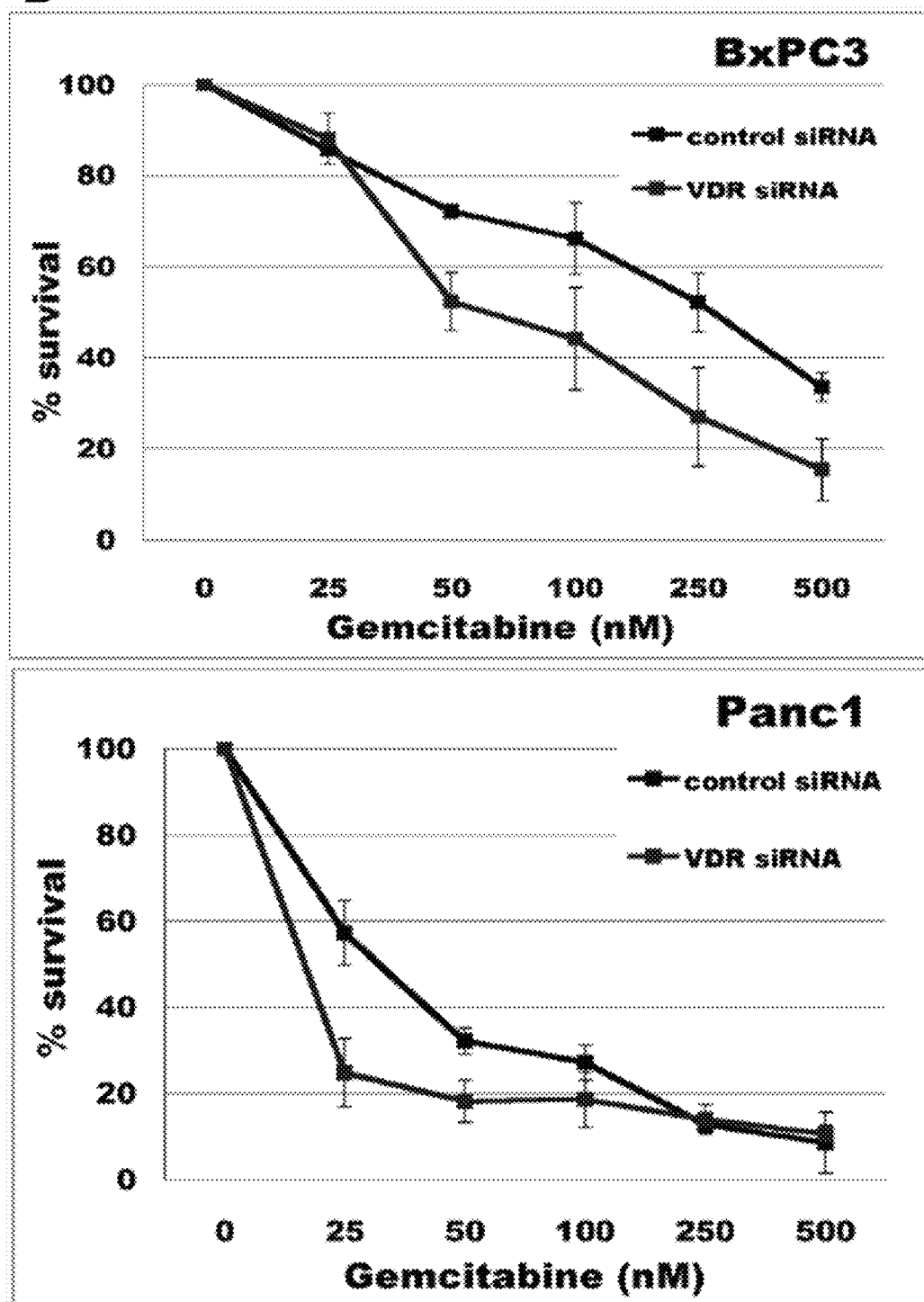
Figure 1:
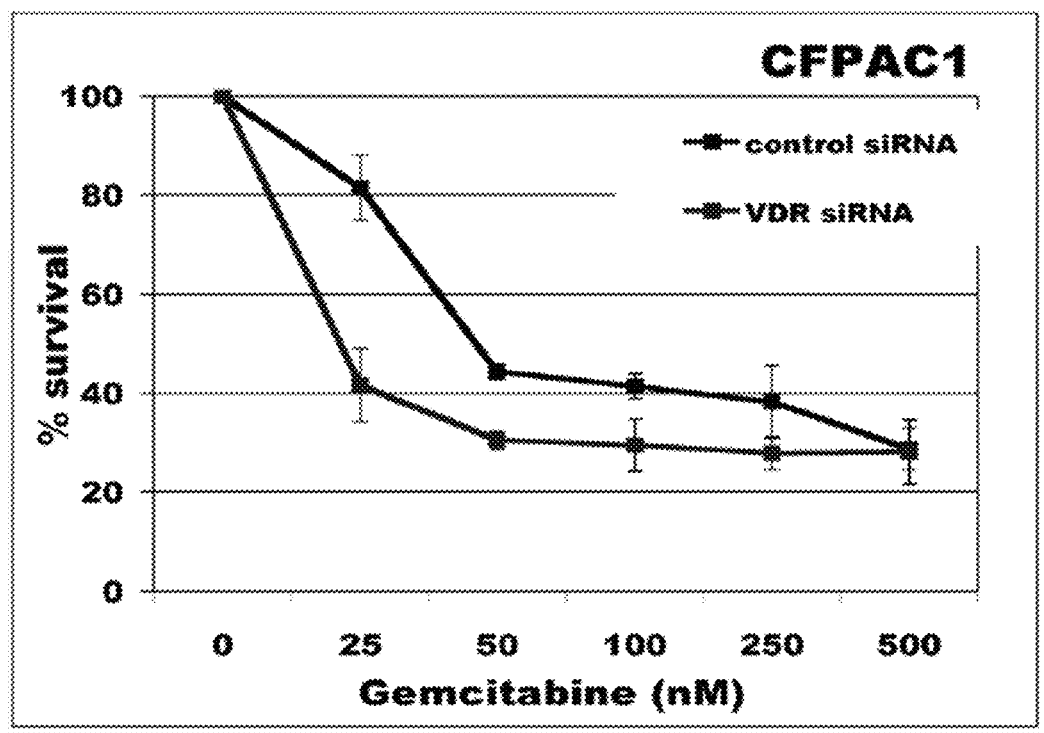
Figure 1:
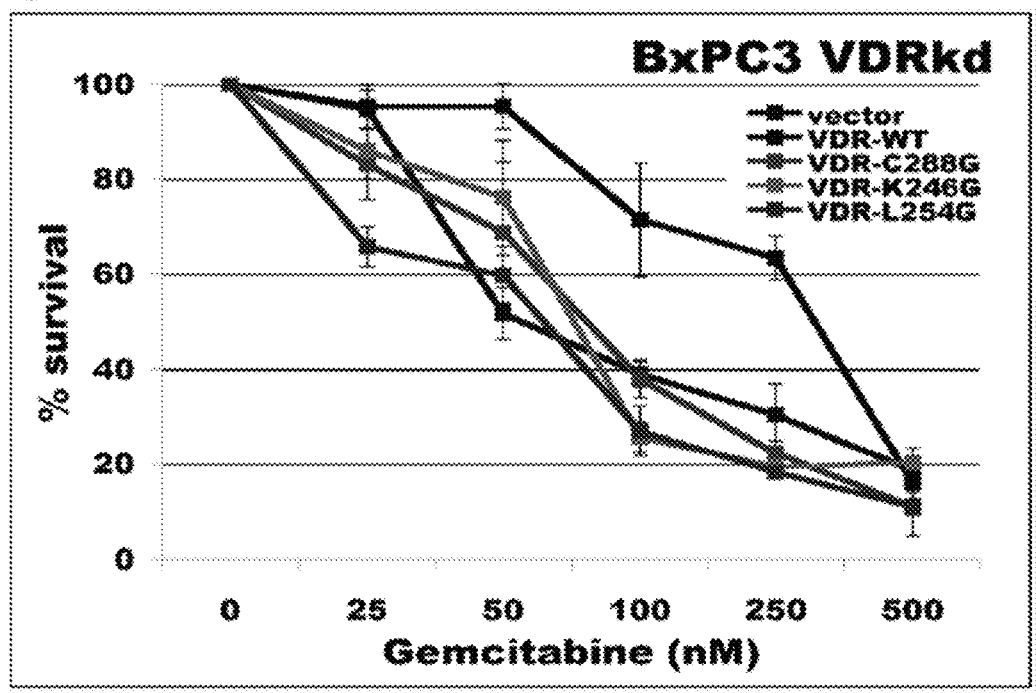
Figure 1:
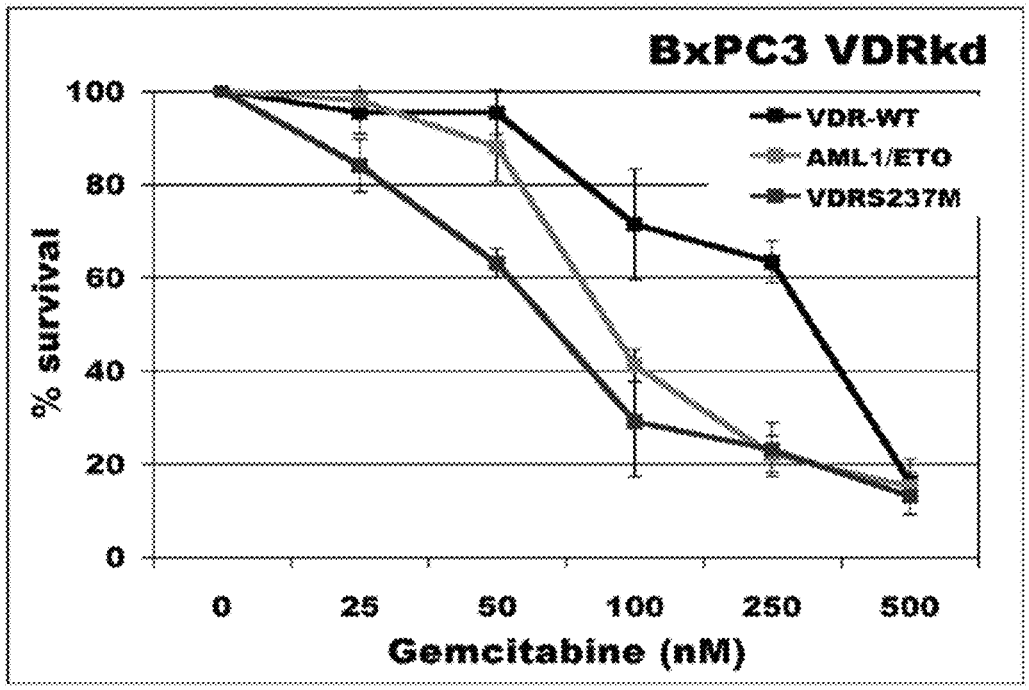
Figure 1:
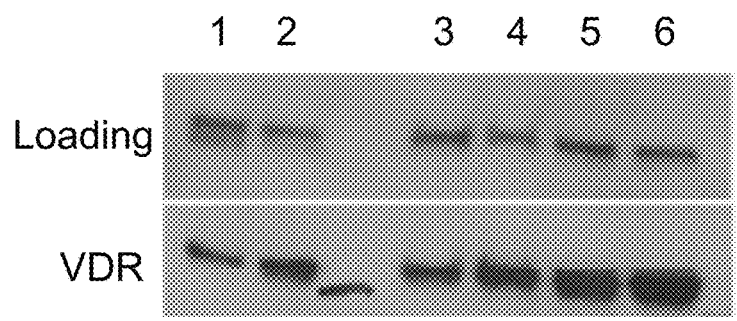
Figure 1:
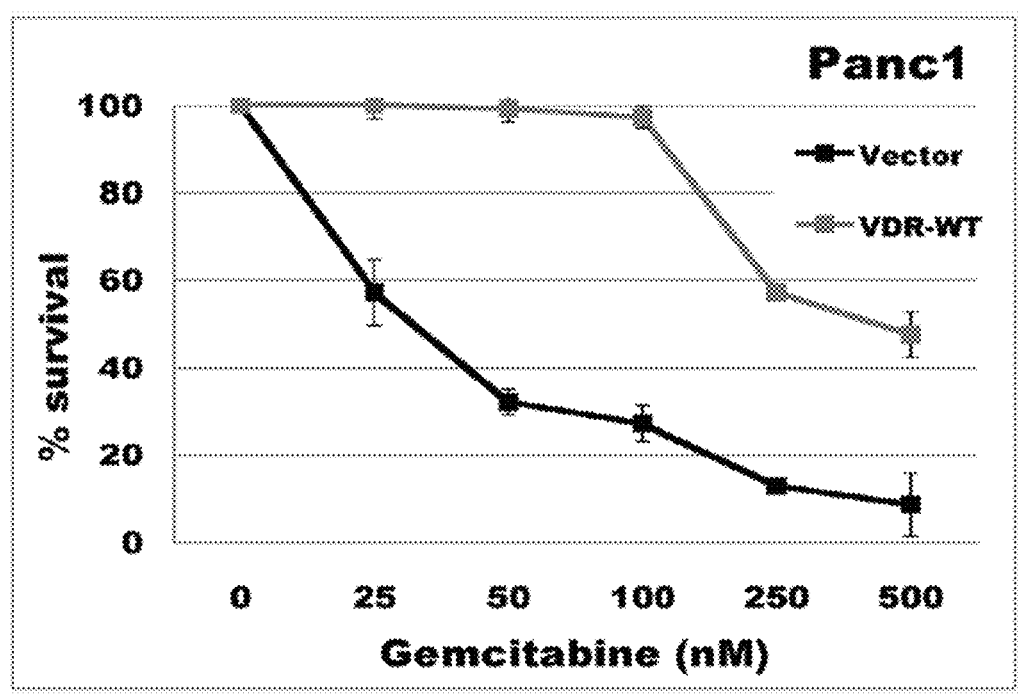

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

Knockdown includes the reduced expression of a gene. A knockdown typically has at least about a 20% reduction in expression, preferably has at least about a 50% reduction in expression, and more preferably has at least about a 75% reduction in expression, and in some aspects has at least about an 80% to about an 85% reduction in expression, at least about an 85% to about a 90% reduction in expression, or about an 80% to about a 90% reduction in expression, and in some aspects has a greater than 90% reduction in expression, or a greater than 95% reduction in expression.

Nucleic acid molecules include any chain of at least two nucleotides, which may be unmodified or modified RNA or DNA, hybrids of RNA and DNA, and may be single, double, or triple stranded.

Expression of a nucleic acid molecule includes the biosynthesis of a gene product, including but not limited to the transcription of a gene into RNA, the translation of RNA into a protein or polypeptide, and all naturally occurring post-transcriptional and post-translational modifications thereof.

Inhibiting includes interfering with, reducing, decreasing, blocking, preventing, delaying, inactivating, antagonizing, desensitizing, stopping, knocking down (e.g., knockdown), and/or downregulating the biologic activity or expression of a molecule, such as the vitamin D receptor, or pathway of interest, such as a signal pathway induced or potentiated by vitamin D receptor activation.

It has been observed in accordance with the invention that knockdown of vitamin D receptor (VDR) expression, or chemical inactivation of this receptor in cancer cells enhances sensitization of the cells to inhibition of PARP-1, with the result of synergistically-enhanced tumoricidal activity observed in tumor cells treated with this combination therapy, relative to tumor cells treated with either VDR inhibition or PARP-1 inhibition by itself. It has been further observed that the VDR plays a role in homologous recombination. Homologous recombination plays a role in the repair of double stranded DNA breaks. Thus, inhibition of homologous recombination-based double stranded DNA break repair via the VDR makes cancer cells more susceptible to PARP inhibition therapy, in line with the observation that the efficacy of PARP inhibitors depends on cells having a diminished or no capacity to carry out homologous recombination. Of note, inactivating the VDR runs contrary to the conventional understanding in the cancer treatment art because it has been established that vitamin D has antiproliferative properties such that the vitamin D receptor itself plays a positive role in cancer treatment. Under the conventional understanding, any knockdown or inhibition of the vitamin D receptor would be expected to have a deleterious effect on cancer therapy. Accordingly, the invention features methods for treating tumors comprising cells expressing the vitamin D receptor. The methods may be carried out in vivo, ex vivo, in vitro, or in situ.

In some aspects, a method for treating a tumor comprises contacting tumor cells with an effective amount of a vitamin D receptor ligand and contacting the cells with an effective amount of an inhibitor or PARP-1. The combination of the VDR ligand and PARP-1 inhibitor produces a therapeutic synergy in killing the tumor cells relative the killing of the tumor cells induced by either the ligand or the PARP-1 inhibitor alone. Cell death may be enhanced in tumors resistant to PARP-1 inhibitor therapy.

In some aspects, a method for treating a tumor comprises inhibiting the expression of a constituent of the vitamin D receptor signaling pathway in the cells and contacting the cells with an effective amount of a PARP-1 inhibitor. The constituent may be one or more of retinoid receptor X (RXR), runt related transcription factor 2 (RUNX2), and zinc finger and BTB domain containing 16 (ZBT16). This latter gene is a member of the Krueppel C2H2-type zinc-finger protein family and encodes a zinc finger transcription factor that contains nine Kruppel-type zinc finger domains at the carboxyl terminus. In preferred aspects, inhibiting the expression of the constituent of the vitamin D receptor signaling pathway in the cells enhances the level of PARP inhibitor-induced cell death in the tumor relative to the level of cell death in a tumor of the same type contacted with the PARP inhibitor in which the expression of the constituent was not inhibited.

In any of the methods, the expression of the vitamin D receptor or a constituent of the vitamin D receptor signaling pathway can be inhibited, for example, by transfecting tumor cells with a nucleic acid molecule that interferes with the expression of the gene encoding the vitamin D receptor or a nucleic acid molecule that interferes with the expression of the gene encoding the constituent of the vitamin D receptor signaling pathway such as RXR, RUNX2, and ZBTB16. Gene expression can be inhibited, for example, through the use of a variety of post-transcriptional gene silencing (RNA silencing) techniques.

RNA interference (RNAi) is a mechanism of post-transcriptional gene silencing mediated by double-stranded RNA (dsRNA), which is distinct from antisense and ribozyme-based approaches. RNA interference may be effectuated, for example, by administering a nucleic acid (e.g., dsRNA) that hybridizes under stringent conditions to the gene encoding the vitamin D receptor, thereby attenuating its expression. RNA interference provides shRNA or siRNA that comprise multiple sequences that target one or more regions of the target gene. dsRNA molecules (shRNA or siRNA) are believed to direct sequence-specific degradation of mRNA in cells of various types after first undergoing processing by an RNase III-like enzyme called DICER into smaller dsRNA molecules comprised of two 21 nucleotide (nt) strands, each of which has a 5' phosphate group and a 3' hydroxyl, and includes a 19 nt region precisely complementary with the other strand, so that there is a 19 nt duplex region flanked by 2 nt-3' overhangs. RNAi is thus mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides. In mammalian cells, dsRNA longer than approximately 30 nucleotides typically induces nonspecific mRNA degradation via the interferon response. However, the presence of siRNA in mammalian cells, rather than inducing the interferon response, results in sequence-specific gene silencing.

Viral vectors or DNA vectors encode short hairpin RNA (shRNA) which are processed in the cell cytoplasm to short interfering RNA (siRNA). In general, a short, interfering RNA (siRNA) comprises an RNA duplex that is preferably approximately 19 basepairs long and optionally further comprises one or two single-stranded overhangs or loops. A siRNA may comprise two RNA strands hybridized together, or may alternatively comprise a single RNA strand that includes a self-hybridizing portion. siRNAs may include one or more free strand ends, which may include phosphate and/or hydroxyl groups. siRNAs typically include a portion that hybridizes under stringent conditions with a target transcript. One strand of the siRNA (or, the self-hybridizing portion of the siRNA) is typically precisely complementary with a region of the target transcript (e.g., vitamin D receptor transcript), meaning that the siRNA hybridizes to the target transcript without a single mismatch. In aspects in which perfect complementarity is not achieved, it is generally preferred that any mismatches be located at or near the siRNA termini.

siRNAs have been shown to downregulate gene expression when transferred into mammalian cells by such methods as transfection, electroporation, cationic liposome-mediated transfection, or microinjection, or when expressed in cells via any of a variety of plasmid-based approaches. The siRNA may comprise two individual nucleic acid strands or of a single strand with a self-complementary region capable of forming a hairpin (stem-loop) structure. A number of variations in structure, length, number of mismatches, size of loop, identity of nucleotides in overhangs, etc., are consistent with effective siRNA-triggered gene silencing. While not wishing to be bound by any theory, it is believed that intracellular processing (e.g., by DICER) of a variety of different precursors results in production of siRNA capable of effectively mediating gene silencing. Generally, it is preferred to target exons rather than introns, and it may also be preferable to select sequences complementary to regions within the 3' portion of the target transcript. Generally it is preferred to select sequences that contain an approximately equimolar ratio of the different nucleotides and to avoid stretches in which a single residue is repeated multiple times.

siRNAs may thus comprise RNA molecules having a double-stranded region approximately 19 nucleotides in length with 1-2 nucleotide 3' overhangs on each strand, resulting in a total length of between approximately 21 and 23 nucleotides, siRNAs also include various RNA structures that may be processed in vivo to generate such molecules. Such structures include RNA strands containing two complementary elements that hybridize to one another to form a stem, a loop, and optionally an overhang, preferably a 3' overhang. Preferably, the stem is approximately 19 bp long, the loop is about 1-20, more preferably about 4-10, and most preferably about 6-8 nt long and/or the overhang is about 1-20, and more preferably about 2-15 nt long. In certain aspects, the stem is minimally 19 nucleotides in length and may be up to approximately 29 nucleotides in length. Loops of 4 nucleotides or greater are less likely subject to steric constraints than are shorter loops and therefore may be preferred. The overhang may include a 5' phosphate and a 3' hydroxyl. The overhang may, but need not comprise a plurality of U residues, e.g., between 1 and 5 U residues. Classical siRNAs as described above trigger degradation of mRNAs to which they are targeted, thereby also reducing the rate of protein synthesis. In addition to siRNAs that act via the classical pathway, certain siRNAs that bind to the 3' UTR of a template transcript may inhibit expression of a protein encoded by the template transcript by a mechanism related to but distinct from classic RNA interference, e.g., by reducing translation of the transcript rather than decreasing its stability. Such RNAs are referred to as microRNAs (miRNAs) and are typically between approximately 20 and 26 nucleotides in length, e.g., 22 nt in length. It is believed that they are derived from larger precursors known as small temporal RNAs (stRNAs) or mRNA precursors, which are typically approximately 70 nt long with an approximately 4-15 nt loop. Endogenous RNAs of this type have been identified in a number of organisms including mammals, suggesting that this mechanism of post-transcriptional gene silencing may be widespread. MicroRNAs have been shown to block translation of target transcripts containing target sites.

siRNAs such as naturally occurring or artificial (i.e., designed by humans) mRNAs that bind within the 3' UTR (or elsewhere in a target transcript) and inhibit translation may tolerate a larger number of mismatches in the siRNA/template duplex, and particularly may tolerate mismatches within the central region of the duplex. In fact, there is evidence that some mismatches may be desirable or required as naturally occurring stRNAs frequently exhibit such mismatches as do mRNAs that have been shown to inhibit translation in vitro. For example, when hybridized with the target transcript such siRNAs frequently include two stretches of perfect complementarity separated by a region of mismatch. A variety of structures are possible. For example, the mRNA may include multiple areas of nonidentity (mismatch). The areas of nonidentity (mismatch) need not be symmetrical in the sense that both the target (e.g., the vitamin D receptor, vitamin D receptor signal pathway constituent, or mutant p53) and the mRNA include non-paired nucleotides. Typically the stretches of perfect complementarity are at least 5 nucleotides in length, e.g., 6, 7, or more nucleotides in length, while the regions of mismatch may be, for example, 1, 2, 3, or 4 nucleotides in length.

Hairpin structures designed to mimic siRNAs and mRNA precursors are processed intracellularly into molecules capable of reducing or inhibiting expression of target transcripts (e.g., the vitamin D receptor, vitamin D receptor signal pathway constituent, or mutant p53). These hairpin structures, which are based on classical siRNAs consisting of two RNA strands forming a 19 bp duplex structure are classified as class I or class II hairpins. Class I hairpins incorporate a loop at the 5' or 3' end of the antisense siRNA strand (i.e., the strand complementary to the target transcript whose inhibition is desired) but are otherwise identical to classical siRNAs. Class II hairpins resemble mRNA precursors in that they include a 19 nt duplex region and a loop at either the 3' or 5' end of the antisense strand of the duplex in addition to one or more nucleotide mismatches in the stem. These molecules are processed intracellularly into small RNA duplex structures capable of mediating silencing. They appear to exert their effects through degradation of the target mRNA rather than through translational repression as is thought to be the case for naturally occurring mRNAs and stRNAs.

Thus, a diverse set of RNA molecules containing duplex structures is able to mediate silencing through various mechanisms. Any such RNA, one portion of which binds to a target transcript (e.g., the vitamin D receptor, vitamin D receptor signal pathway constituent, or mutant p53) and reduces its expression, whether by triggering degradation, by inhibiting translation, or by other means, may be considered an siRNA, and any structure that generates such an siRNA (i.e., serves as a precursor to the RNA) is useful.

A further method of RNA interference is the use of short hairpin RNAs (shRNA). A plasmid containing a DNA sequence encoding for a particular desired siRNA sequence is delivered into a target cell via transfection or virally-mediated infection. Once in the cell, the DNA sequence is continuously transcribed into RNA molecules that loop back on themselves and form hairpin structures through intramolecular base pairing. These hairpin structures, once processed by the cell, are equivalent to transfected siRNA molecules and are used by the cell to mediate RNAi of the desired protein. The use of shRNA has an advantage over siRNA transfection as the former can lead to stable, long-term inhibition of protein expression. Inhibition of protein expression by transfected siRNAs is a transient phenomenon that does not occur for times periods longer than several days. In some cases, though, this may be preferable and desired. In cases where longer periods of protein inhibition are necessary, shRNA mediated inhibition is preferable. The use of shRNA is preferred for some aspects of the invention. Typically, siRNA-encoding vectors are constructs comprising a promoter, a sequence of the target gene to be silenced in the sense orientation, a spacer, the antisense of the target gene sequence, and a terminator.

Inhibition of the expression of the vitamin D receptor, a vitamin D receptor signal pathway constituent, or mutant p53 can also be effectuated by other means that are known and readily practiced in the art. For example, antisense nucleic acids can be used. Antisense RNA transcripts have a base sequence complementary to part or all of any other RNA transcript in the same cell. Such transcripts modulate gene expression through a variety of mechanisms including the modulation of RNA splicing, the modulation of RNA transport and the modulation of the translation of mRNA. Accordingly, in certain aspects, inhibition of the expression of the vitamin D receptor in a cell can be accomplished by expressing an antisense nucleic acid molecule in the cell.

Antisense nucleic acids are generally single-stranded nucleic acids (DNA, RNA, modified DNA, or modified RNA) complementary to a portion of a target nucleic acid (e.g., an mRNA transcript) and therefore able to bind to the target to form a duplex. Typically, they are oligonucleotides that range from 15 to 35 nucleotides in length but may range from 10 up to approximately 50 nucleotides in length. Binding typically reduces or inhibits the expression of the target nucleic acid, such as the gene encoding the target signal protein. For example, antisense oligonucleotides may block transcription when bound to genomic DNA, inhibit translation when bound to mRNA, and/or lead to degradation of the nucleic acid. Inhibition of the expression of the vitamin D receptor, a vitamin D receptor signal pathway constituent, or mutant p53 can be achieved by the administration of antisense nucleic acids comprising sequences complementary to those of the mRNA that encodes the vitamin D receptor, the vitamin D receptor signal pathway constituent, or mutant p53.

Antisense oligonucleotides can be synthesized with a base sequence that is complementary to a portion of any RNA transcript in the cell. Antisense oligonucleotides can modulate gene expression through a variety of mechanisms including the modulation of RNA splicing, the modulation of RNA transport and the modulation of the translation of mRNA. Various properties of antisense oligonucleotides including stability, toxicity, tissue distribution, and cellular uptake and binding affinity may be altered through chemical modifications including (i) replacement of the phosphodiester backbone (e.g., peptide nucleic acid, phosphorothioate oligonucleotides, and phosphoramidate oligonucleotides), (ii) modification of the sugar base (e.g., 2'-O-propylribose and 2'-methoxyethoxyribose), and (iii) modification of the nucleoside (e.g., C-5 propynyl U, C-5 thiazole U, and phenoxazine C).

Inhibition of the vitamin D receptor or vitamin D receptor signal pathway constituent can also be effectuated by use of ribozymes. Certain nucleic acid molecules referred to as ribozymes or deoxyribozymes have been shown to catalyze the sequence-specific cleavage of RNA molecules. The cleavage site is determined by complementary pairing of nucleotides in the RNA or DNA enzyme with nucleotides in the target RNA. Thus, RNA and DNA enzymes can be designed to cleave to any RNA molecule, thereby increasing its rate of degradation.

Gene expression may also be accomplished using CRISPR/Cas9 targeted genome editing. This uses a short RNA that is complementary to the gene of interest, for example, the VDR gene. The cas9 nuclease recognizes the region of complementarity, cuts the DNA (the genomic locus) and error-prone repair will introduce frameshift mutations that effectively inactivate the gene. This introduces a permanent mutation at the genomic level, and is thus permanent—as opposed to the other technologies that wane overtime because the mRNA is constantly being made.

In some aspects, the cells can be specifically transformed with transcription-silencing nucleic acids such as shRNA or siRNA, or can be transformed with vectors encoding such nucleic acids such that the cell expresses the inhibitory nucleic acid molecules. Transformation of the cells can be carried out according to any means suitable in the art.

A cell can be transfected with such nucleic acid molecules according to any means available in the art such as those describe or exemplified herein. It is preferred that cells are stably transfected with a vector comprising a nucleic acid sequence encoding such regulatory nucleic acid molecules, although transiently transformations are suitable. Any vector suitable for transfection of the particular cell of interest can be used. In preferred embodiments, the vector is a viral vector. In some embodiments, the viral vector is a lentivirus vector.

The biologic activity of the vitamin D receptor, the vitamin D receptor signal pathway constituent, or mutant p53 can be inhibited, for example, by contacting tumor cells with a compound, biomolecule, or composition of a compound or a biomolecule that inhibits, inactivates, or antagonizes the biologic activity of the vitamin D receptor, the vitamin D receptor signal pathway constituent, or mutant p53 in the cell. Preferred biomolecules include peptide inhibitors and antibodies.

Non-limiting examples of compounds/agents that inhibit the biological activity of the vitamin D receptor and/or its signal pathway include vitamin D receptor ligands, including vitamin D analogs and vitamin D3 analogs that antagonize the vitamin D receptor in ways that enhance sensitivity of cells to PARP inhibitors. The ligand may be a vitamin D analog. The vitamin D receptor ligand may be an antagonist of the vitamin D receptor. The ligand may comprise calcitriol, calcipotriol, eldecalcitol, lisinopril, elocalcitol, paricalcitol, seocalcitol, or any combination thereof. The ligand may comprise TEI-9647, TEI-9648, or a derivative or analog thereof. Other suitable agents or analogs include those described in Saito N et al. (2006) Chem. Biochem. 7:1478-90; Deeb K K et al. (2007) Nature 7:684-700; Chiang K-C et al. (2009) World J. Gastroenterol. 15:3349-54, including 1-alpha,25-Dihydroxyvitamin D3 (aka 1α,25(OH)$_2$D$_3$ or calcitriol), 2beta-(3-hydroxypropoxy)-1a,25(OH)$_2$D$_3$ (ED-71 or eldecalcitol), lisinopril, elocalcitol, paricalcitol (19-nor-1alpha, 25(OH)$_2$D$_2$), seocalcitol (EB 1089), ILX23-7553, 22-oxa-1,25-dihydroxyvitamin D3 (OCT), or any combination thereof. Calcitriol is preferred in some aspects. Paricalcitrol is preferred in some aspects. In some aspects, the VDR may be agonized instead of antagonized, provided that agonism of the VDR inhibits homologous recombination in the cell.

Without intending to be limited to any particular theory or mechanism of action, it is believed that tumor cells may express their own ligand that binds to the VDR and directs DNA repair, for example, via homologous recombination. Thus, to the extent a tumor cell expresses such a ligand, the VDR ligand used in accordance with the invention may competitively inhibit this tumor cell ligand, in terms of VDR binding and/or activation or potentiation.

The methods thus relate to a combination treatment, including the VDR ligand and the PARP-1 inhibitor. It is preferred that the vitamin D receptor ligand negatively affects the homologous recombination processes, e.g., inhibits it sufficiently for the PARP inhibitor to be efficacious in inducing tumor cell killing. For the combination, the cells may be contacted with the PARP inhibitor before the ligand, substantially contemporaneously with the ligand, or preferably, after the ligand. The combination of the VDR ligand and PARP inhibitor produces a therapeutic synergy in killing tumor cells and in treating tumors. The synergy is greater than the therapeutic effect of either the VDR ligand or the PARP inhibit or alone.

In some aspects, the methods further comprise inducing DNA damage, for example, double stranded DNA breaks, in the DNA of the tumor cells. The damage may be induced in chromosomal DNA. Thus, the combination of DNA damage such as double stranded breaks along with the inhibited/impaired homologous recombination owing to the inactivation of the vitamin D receptor may make the cells more susceptible to PARP inhibition. DNA damage may be induced according to any suitable means, including, for example, by irradiating tumor cells, or by contacting the cells with a DNA damage-inducing agent. The DNA damage-inducing agent may be a platinum-based chemotherapeutic agent. The DNA damage-inducing agent may comprise gemcitabine. The combination of the VDR ligand, DNA damage such as double stranded breaks, and PARP inhibitor produces a therapeutic synergy in killing tumor cells and in treating tumors. The synergy is greater than the therapeutic effect of the VDR ligand, DNA damage, or PARP inhibition alone.

The methods may be used to treat any cancer (or tumor type) in which the vitamin D receptor is expressed, or expressed at abnormal levels, or in which vitamin D receptor signaling mediates cancer development, progression, pathology, or resistance to one or more chemotherapeutic agents. Non-limiting examples of such cancers include pancreatic cancer, lung cancer (including non small cell lung cancer), bladder cancer, breast cancer, ovarian cancer esophageal cancer, prostate cancer, and lymphoma, among others, including any of these cancers in a metastatic stage. Pancreatic cancer is a highly preferred target of the methods.

The invention also features methods for treating a malignancy of the pancreas, lung, bladder, prostate gland, breast, ovary, lymph nodes, or esophagus comprising cells expressing the vitamin D receptor. In some aspects, the methods comprise transfecting a malignant cell of the pancreas, lung, bladder, prostate, breast, ovary, lymph nodes, or esophagus in the subject with a nucleic acid molecule that interferes with the expression of the vitamin D receptor, and administering to the subject an effective amount of a PARP-1 inhibitor. Transfection of the cells may be facilitated according to any technique suitable in the art.

In some aspects, the methods comprise administering to a subject in need thereof an effective amount of a nucleic acid molecule that interferes with the expression of the vitamin D receptor and administering to the subject an effective amount of a PARP-1 inhibitor. Following administration of the nucleic acid molecule, the nucleic acid molecule transfects a malignant cell of the pancreas, lung, bladder, breast, ovary, prostate, lymph nodes, or esophagus expressing the vitamin D receptor and interferes with the expression of the gene encoding the vitamin D receptor. The nucleic acid molecule may be administered to or specifically targeted to the cells of interest, or at least to an area proximal to the cells of interest. Transfection of the cells may be facilitated according to any technique suitable in the art.

In some aspects, the methods comprise administering to a subject in need thereof an effective amount of a vitamin D receptor ligand and an effective amount of a PARP inhibitor. The ligand may be a vitamin D analog. The vitamin D receptor ligand may be an antagonist of the vitamin D receptor. The ligand may comprise calcitriol, calcipotriol, eldecalcitol, lisinopril, elocalcitol, paricalcitol, seocalcitol, or any combination thereof. The ligand may comprise TEI-9647, TEI-9648, OU-72, or a derivative or analog thereof. The PARP-1 inhibitor may comprise olaparib, iniparib, rucaparib, veliparib, MK 4827, BMN673, BSI 401, or any combination thereof. The methods may further comprise inducing DNA damage in tumor cells in the subject, for example, via irradiating the tumor cells or by administering to the subject an amount of gemcitabine effective to induce DNA damage in the tumor cells. DNA damage preferably comprises double stranded DNA breaks.

The agents (ligands, PARP inhibitors, gemcitabine, etc.) may be administered according to any technique suitable in the art. The subject to which the agents are administered may be any animal, preferably mammals, and including laboratory animals (e.g., rodents such as mice, rabbits, and rats), companion animals (e.g. cats and dogs), farm animals (e.g., horses, cows, pigs, sheep), and non-human primates. Human beings are preferred subjects.

RAD51 is a protein related to DNA repair. RAD51 protein localizes to sites of DNA damage. It has been observed in accordance with the invention that inhibition of the vitamin D receptor also blocks RAD51-mediated DNA damage repair. RAD51 may thus serve as a biomarker for vitamin D receptor inhibition. In particular, lack of RAD51 localization to regions of DNA damage may signal the loss of vitamin D receptor expression or biologic activity. Lack of RAD51 localization to regions of DNA damage may signal inhibition of vitamin D receptor expression or biologic activity.

The following examples are provided to describe the invention in greater detail. They are intended to illustrate, not to limit, the invention.

Example 1

Materials and Methods

Cell culture and chemicals. Panc1, BxPC3, and CFPAC1 cells were purchased from American Type Culture Collection (ATCC) and banked in house until use. Cell lines were cultured in DMEM/10% FBS supplemented with 2 mM glutamine and 1% penicillin, streptomycin, and kanamycin (PSK) and were maintained at 37° C. in 5% $CO_2$. Charcoal stripped (in house cell culture facility) and dialyzed FBS (Life Technologies; 509 26400-036) were used. Gemcitabine was obtained from the in house pharmacy. Rucaparib and trichostatin A were gifts.

Plasmids. pLKO.1-VDRshRNA was purchased from Thermo Scientific (TRCN0000019504). pCMV-WT-VDR and pCMV-AML1/ETO plasmids were made from backbones obtained from Addgene. The VDR-S237M mutant was a gift. To create the RNAi resistant allele, pCMV-WT-VDR was mutated at the VDR shRNA target sequence with conservative mutations at the wobble position of 4 consecutive codons. VDR-C288G, K246G, and L254G mutants were created by Quick Change II mutagenesis (Agilent Technologies; 520 200521).

Synthetic lethal RNAi Screen. High throughput RNAi was performed using the validated human genome-wide siRNA library version 2.0 obtained from Dharmacon. This is a SMARTPool (4 siRNAs per gene) library that targeted ~23,500 of the annotated genes, and has been validated to deplete mRNA by 75%. Stock siRNA was diluted in siRNA buffer (Dharmacon; B-002000-UB-100) and 10 ng of siRNA was reverse transfected into Panc1 cells seeded into white Corning 384-well plates (Fisher Scientific; 07-201-320) in quadruplicates on day 0. Briefly, diluted Dharmafect1 reagent (Dharmacon; T-2001-01) in OptiMEM (Life Technologies; 51985091) was added to the wells and allowed to complex with siRNA for 20 minutes at room temperature. Panc1 cells in 100 μl of DMEM/10% FBS media without PSK were mixed with 100 μl of transfection mix at 1000 cells/well. Plates were incubated at 37° C. with 5% $CO_2$. After 48 hours, either vehicle or gemcitabine (50 nM) was added and plates were further incubated for 48 hours. Total viable cell number was determined by the addition of Cell Titer Glo (Promega; G7573) and relative luminescence units (RLU) were measured using an EnVision plate reader (Perkin Elmer). Raw RLU data was normalized to the mean siRNA control on each plate. The effect of gemcitabine treatment on viability was measured based on the normalized viabilities in the drug treated and vehicle wells using Limma, Statistical significance was measured by p-values controlled for the false discovery rate (FDR) using the Benjamini-Hochberg step-up method to account for multiple testing. Hits showing an FDR of less than 20% and also a change of at least 15% in viability relative to vehicle treated cells were selected for validation.

RNAseq data analysis. Raw sequence reads were aligned to the human hg19 genome using the Tophat algorithm; Cufflinks algorithm was implemented to assemble transcripts and estimate their abundance. Cuffdiff was used to statistically assess expression changes in quantified genes in different conditions.

Cell viability assays. For clonogenic assays, 1000 cells per well were seeded into 6 well plates on day 0. Cells were treated with gemcitabine at various doses on day 1 for 24 hours, Gemcitabine was washed out on day 2, and cells were allowed to grow for a subsequent 10 days before being fixed (10% methanol+10% acetic acid) and stained with crystal violet (0.4% in 20% ethanol) for colony counting and quantitation. For Rucaparib clonogenic assays, the drug was added at various doses 24 hours after cell plating, and cells were allowed to grow for a subsequent 10 days in the presence of Rucaparib. For TSA clonogenic assays, the drug was added for 4 hours prior to addition of gemcitabine or vehicle for another 18 hours before drugs were washed away, and cells were allowed to grow in drug-free medium for 10 days.

Microscopy. For timelapse studies, Panc1 cells with stable expression of Histone H2B fused at its C-terminus to GFP were seeded into 6-well plates. 24 hours post cell plating, gemcitabine (50 nM) was added before timelapse was commenced. The plate was placed in a 37° C. chamber; bright-field and fluorescent images were taken every 5 minutes for 48 hours using a Nikon TE2000S microscope controlled by Metamorph (Molecular Devices). Three independent movies were conducted for each condition. Movies were allowed to commence for 48 hours for each independent experiment.

For Immunofluorescence, cells were plated onto coverslips 24 hours pre-gemcitabine treatment. At different timepoints post gemcitabine treatment, cells were permeablized, fixed (4% paraformaldehyde) and stained. Antibodies to γH2AX (Millipore; 05-636), Rad51 (a gift), and 53BP1 were used. Alexa Fluor-conjugated (488, 555, and 647 nm) secondary antibodies (Molecular probes; A-11029, A-21428, A-21247) were used at a final concentration of 1 and nuclei counterstained with DAPI. Images were captured using a 40× or 63× high NA objective mounted on a semi-automated inverted microscope (Nikon TEi) with a charge-coupled device camera (Photometrics1394) using Nikon Elements 2.0. Exposure times for antibodies were optimized for control samples and identical exposure times used for the experimental samples. Images were quantitated and analyzed using Nikon Elements 2.0. Confocal images were taken using a Leica TCS-SP8 microscope controlled by LAS software (Leica Microsystems).

Western Blotting. BxPC3, Panc1, and CFPAC1 cells were treated with vehicle or gemcitabine (50 nM) for 18 hrs. Cells were harvested, washed in PBS and lysed in NP40 lysis buffer (1% NP40/PBS/10% glycerol) with protease and phosphatase inhibitors. Protein concentrations were determined with MicroBCA Assay (Pierce Biotechnology; 23224 and 23228) and then SDS sample buffer was added to the lysates. 40 μg of boiled lysates was separated by SDS-PAGE and then transferred onto Immobilon P membrane (Millipore; IPVH00010). Antibodies used for immunoblotting were obtained from: VDR (Epitomics; 3277-1), γH2AX (Upstate Biotechnologies, now Millipore; 05-636), Rad51 (Genetex; GTX70230, gift), p300 (Santa Cruz Biotechnologies; SC-584), and TAO1 kinase (Bethyl Labs; A300-524A). TAO1 was used as a loading control since its expression did not vary in any cell lines or drug treatments.

Example 2

RNAi Synthetic Lethality Screen to Enhance Gemcitabine Sensitivity

A genome-wide siRNA screen was performed to identify genes and pathways in Panc1 pancreatic adenocarinoma cells that can be targeted for gemcitabine sensitization. A sublethal dose ($IC_{20}$) of gemcitabine was used (50 nM), which was sufficient to induce an S phase arrest and DNA damage as seen by γH2AX foci. The low dose of gemcitabine (50 nM) may also be clinically relevant as it has been reported that only a small percentage of a chemotherapeutic dose of drugs actually reaches the PCa tumor because of its dense stromal microenvironment.

Two days after siRNA transfection, gemcitabine or vehicle was added to duplicate plates and cell viability was assessed 48 hours later. Values were normalized to internal standards, as each plate contained negative and positive controls, and comparisons made between vehicle and gemcitabine treated samples. Statistical analysis of the data was used to rank the siRNAs according to their ability to enhance gemcitabine killing. The false discovery rate (FDR) was determined for each sample and a cutoff of 0.2 was used to identify 125 primary candidates.

Candidates were further validated for gemcitabine sensitization with a set of deconvolved siRNAs (4 individual siRNAs for each gene). 155 genes were validated based on the ability of >2 of 4 deconvolved siRNAs to enhance gemcitabine killing. The validated hits were subjected to pathway analysis using Ingenuity and STRING databases to assess potential relationships with one another. A major gemcitabine survival network consisted of various DNA damage response genes involved in repair and checkpoint functions (Chk1, Wee1, PIAS4, and 53BP1). This result validated the screen and gave confidence to further evaluate candidates not previously known to be involved in gemcitabine response.

Example 3

The Vitamin D Receptor (VDR) Sensitizes Pancreatic Cancer Cells to Gemcitabine

The Vitamin D Receptor (VDR) is a member of the superfamily of nuclear hormone receptors. Although the role of VDR in drug sensitization has not been documented, there have been reports that suggest a relationship with DNA damage. A positive feedback loop has been reported to exist between the DNA damage checkpoint kinase, ATM, and VDR following DNA damage. Notably, ATM and VDR expression were increased after DSB induction by N-nitroso-N methylurea through ATM phosphorylation of VDR which in turn promoted VDR transactivation of the ATM gene. In addition, Vitamin D3 (1alpha,25(OH)$_2$D$_3$), which is the major ligand of the VDR, has been shown to protect cells from genotoxic stress bypromoting DNA repair. Vitamin D3 (VD3) bound VDR is responsible for clearing cyclobutane pyrimidine dimers (CPDs) and pyrimidone photoproducts in mice that were exposed to UVB. Moreover, topically applied VD3 protected skin from UV induced photodamage.

First, the sensitization achieved with VDR knockdown was compared to that of Chk1 knockdown, a well-known chemosensitization target that overrides the DNA damage checkpoint and promotes mitotic catastrophe. Clonogenic assays were conducted, as this was more sensitive and reliable than the short term viability assays.

Panc1 cells transfected with control, VDR, and Chk1 siRNA's were treated with vehicle or 50 nM gemcitabine for 24 hours before drugs were washed out and cells seeded for clonogenic assays (FIG. 1, A). Colony formation did not differ significantly in control siRNA samples treated with vehicle versus gemcitabine. Compared to control samples treated with gemcitabine, only 8% and 3% of the gemcitabine treated VDR and Chk1 siRNAs transfected cells survived, respectively. Colony formation of 92% and 77% efficiency was seen for vehicle treated VDR and Chk1 siRNAs transfected cells, respectively.

These studies were extended to establish gemcitabine kill curves following control and VDR siRNA transfections of Panc1, BxPC3, and CFPAC1 cells. All three PCa cell lines showed increased sensitivity to gemcitabine after knockdown of VDR (FIG. 1, B). BxPC3 cells treated with control siRNA had a mean IC$_{50}$ of ~200 nM as compared to the mean IC$_{50}$ of ~60 nM after transfection with VDR siRNA (p value of 0.036). CFPAC1 cells treated with control siRNA had a mean IC$_{50}$ of ~45 nM while the IC$_{50}$ of VDR depleted cells was reduced to ~20 nM (p=0.083). Similarly, the IC$_{50}$ of control transfected Panc1 cells was reduced from ~30 nM to ~18 nM after VDR knockdown.

To establish specificity of the VDR siRNA, a rescue of the sensitization was attempted by expressing RNAi resistant alleles of WT-VDR in cells stably knocked down of VDR. A stable VDR knockdown cell line was established by utilizing a lentiviral shRNA delivery system. BxPC3, Panc1, and CFPAC1 cells were infected with virus but only BXPC3 cells that were stably knocked down of VDR were recovered.

Western blots showed that BxPC3 VDRkd cells had ~10 fold reduction of VDR protein compared to the parental BxPC3 cells. Vector and WT-VDR were transfected into the BxPC3 VDRkd cells and tested for gemcitabine sensitivity in clonogenic assays. As with the untransfected cells, vector transfected cells had an IC$_{50}$ of ~50 nM gemcitabine. However, cells transfected with WT-VDR showed increased IC$_{50}$ of ~300 nM gemcitabine (p=0.089) (FIG. 1, C).

To extend these results, various VDR mutants that are unable to activate transcription were tested. Vitamin D3 is the major ligand that binds to VDR to activate transcription. In addition, transcription is usually mediated by a heterodimer of VDR and RXR (retinoid acid X receptor). Mutations that disrupted ligand binding (C288G) and heterodimerization (K246G) (L254G) were transfected into the BxPC3 VDRkd cells but none of them rescued the gemcitabine sensitivity as with WT-VDR (FIG. 1, D). As a further test for VDR specificity, two dominant negative mutants were used to neutralize the ability of WT-VDR to restore gemcitabine resistance to the BXPC3 VDRkd cells. The S237M mutation in VDR prevents binding by vitamin D3 but, unlike other ligand mutants, it exerts a dominant negative effect by titrating away essential binding partners from endogenous VDR.

Additionally, the AML1/ETO fusion oncogene that also sequesters VDR from its binding partners, RXR and Runx2 was used, thus disrupting the formation of VDR transcriptional machinery. When WT-VDR was co-transfected with either the S237M mutant or AML1/ETO into BxPC3 VDRkd cells, colony formation after gemcitabine treatment was reduced when compared to just WT-VDR transfected cells (FIG. 1, D). The IC$_{50}$ for WT-VDR transfected cells was ~260 nM while co-transfection of S237M or AML1/ETO reduced the IC$_{50}$s to ~60 nM (p=0.039) and ~80 nM (p=0.147) respectively, very similar to the IC$_{50}$ for the untransfected VDR knockdown cells. The combined data establish that both the ligand-binding and heterodimerization domains are essential for VDR's role in promoting gemcitabine survival.

Next, the levels of VDR protein were compared in BxPC3, CFPAC1, and Panc1 cells to see if the amount of expression might correlate with gemcitabine sensitivity. Western blots showed that the basal levels of VDR differed amongst the cell lines such that BXPC3 had the highest amounts of VDR, followed by CFPAC1, and then Panc1 cells (FIG. 1, E). After overnight treatment with gemcitabine, VDR levels increased in Panc1 and CFPAC1 cells. No noticeable increase in VDR levels was seen in BXPC3. Comparison of the gemcitabine sensitivity showed that it negatively correlated with VDR levels (FIG. 1, E) such that BxPC3 cells with the highest levels of VDR had a mean IC$_{50}$ of ~200 nM, while CFPAC1 and Panc1 cells had IC$_{50}$'s of ~45 nM and ~30 nM, respectively.

Panc1 cells were used for VDR overexpression experiments to further test the relationship between VDR and gemcitabine sensitivity. Cells transfected with WT-VDR were significantly more resistant to gemcitabine ($IC_{50}$ ~250 nM) than cells transfected with vector ($IC_{50}$ ~25 nM) (FIG. 1, F). The VDR overexpression data supports the VDR knockdown data in establishing that levels of VDR expression is a critical determinant for gemcitabine response in pancreatic cancer cells.

Example 4

Figure 2:
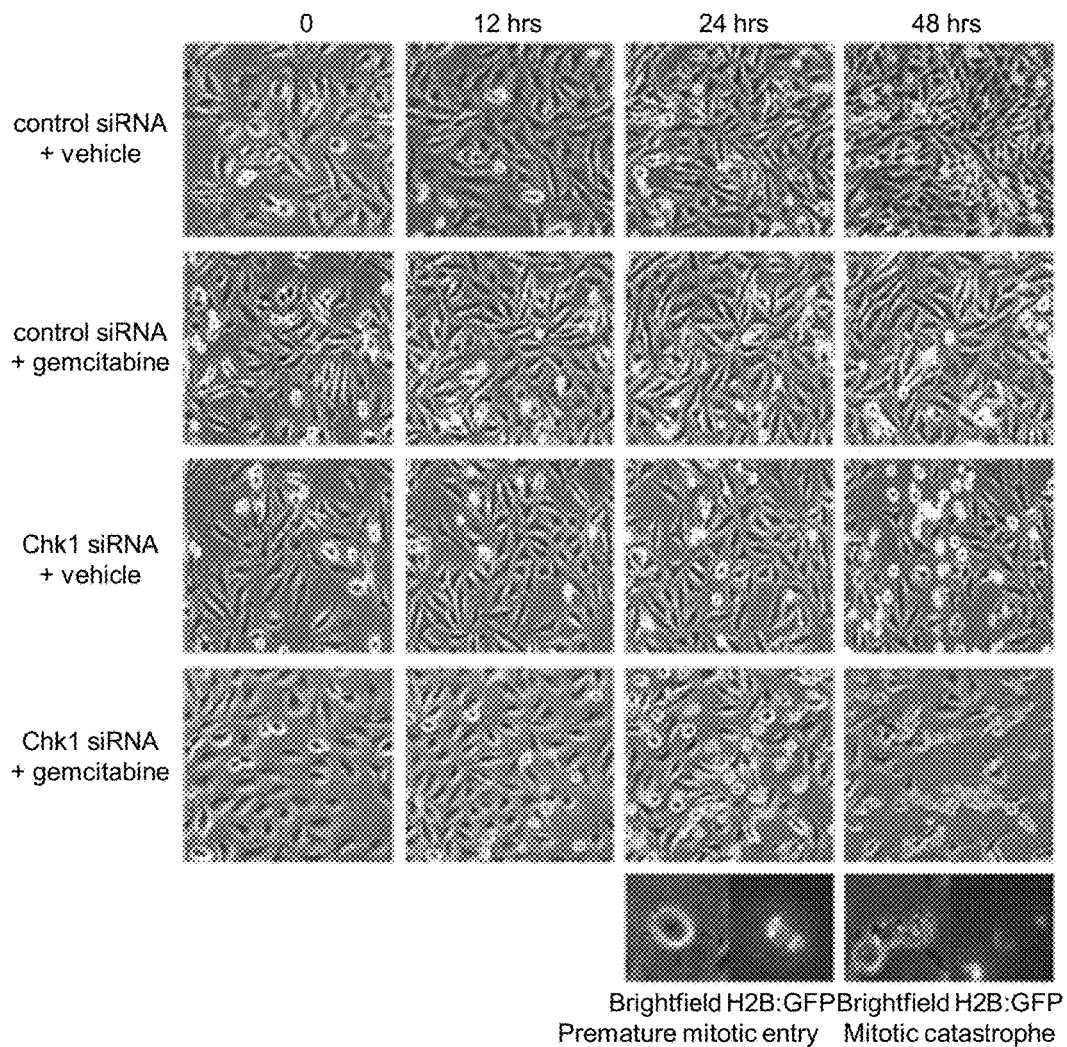
FIG. 2: Gemcitabine sensitization after VDR knockdown is not due to override of the DNA damage checkpoint. Select frames from a 48 hr timelapse of Panc1 cells transfected with control, Chk1, and VDR siRNAs that were treated with vehicle or gemcitabine. Chk1 siRNA of gemcitabine treated samples show increased mitotic cells at later timepoints. Enlarged images show brightfield and gfpH2B images of Chk1 siRNA cells prematurely entering mitosis and undergoing mitotic catastrophe. VDR siRNA transfected cells remain in interphase and die without ever entering mitosis.
Figure 2:
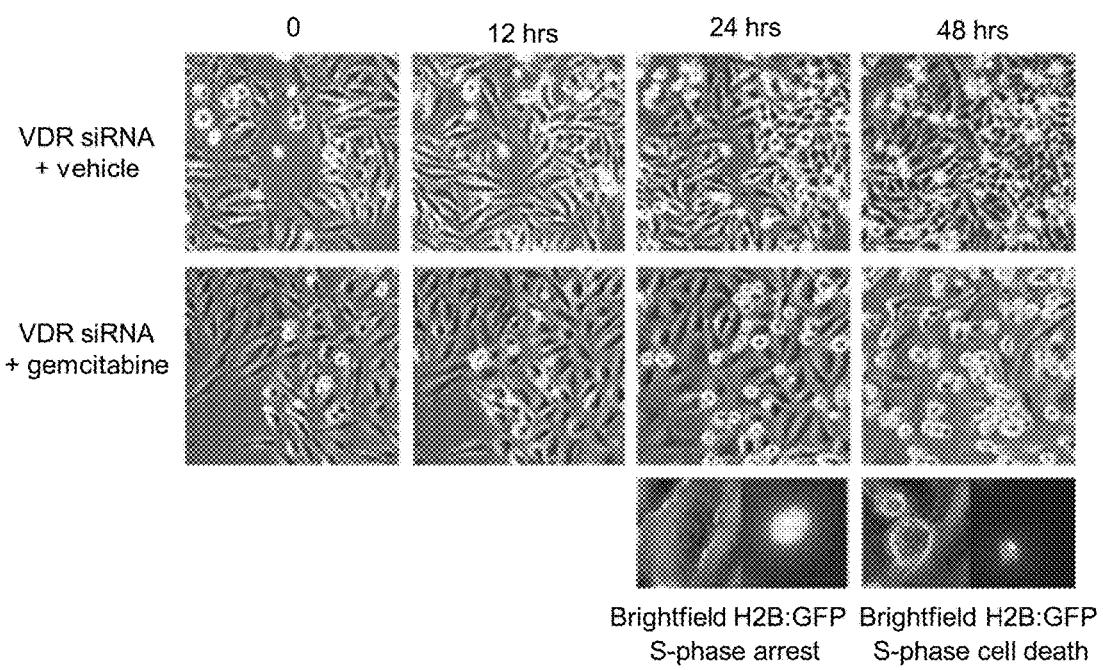

VDR Specifies a Survival Pathway that is Distinct from the DNA Damage Checkpoint Pathway Since VDR knockdown achieved the same degree of gemcitabine sensitization as Chk1 knockdown, it was tested whether the mechanism of VDR sensitization was due to checkpoint override. Time-lapse microscopy was used to track the fates of gemcitabine-treated Panc1 cells that stably expressed a H2B:gfp fusion protein that labeled chromosomes. Cells were transfected with siRNAs, treated with vehicle or gemcitabine and monitored every 10 minutes for 48 hours (FIG. 2).

Control, VDR, or Chk1 siRNAs did not affect viability of vehicle treated cells as their numbers increased at the end of 48 hours. Addition of gemcitabine to control siRNA cells stopped proliferation as a result of the checkpoint, but cells did not die during the span of the timelapse experiment.

Chk1 knockdown abrogated the cell cycle arrest mediated by gemcitabine as cells were observed to enter mitosis where many died or died shortly after exit from mitosis. By contrast, cells transfected with VDR siRNA never entered mitosis, but nevertheless died during the span of the ~48 hour timelapse. It is believed that Gemcitabine sensitization after VDR knockdown is not due to override of the DNA damage checkpoint pathway mediated by Chk1.

Example 5

VDR Knockdown Impairs Foci Formation by DNA Damage Response Proteins Gamma-H2AX, 53BP1, and Rad51 Following Gemcitabine Treatment It was next investigated if drug sensitization after VDR knockdown might be due to defective DNA damage repair. Gemcitabine is a nucleoside analog that acts as a chain terminator that will stall replication forks. If the forks cannot restart, they collapse to form DNA double strand breaks that can be detected by the formation of phospho-γH2AX foci. Repair of stalled forks is mediated by the error-free homologous recombination pathway (HR). Rad51, an essential component of HR, has been implicated in promoting gemcitabine resistance in non-small-cell lung cancer and pancreatic cancer. 53BP1, on the other hand, protects double stranded break ends from resection, which is required for HR, to promote non-homologous end-joining (NHEJ) which is an error-prone repair pathway.

Figure 3:
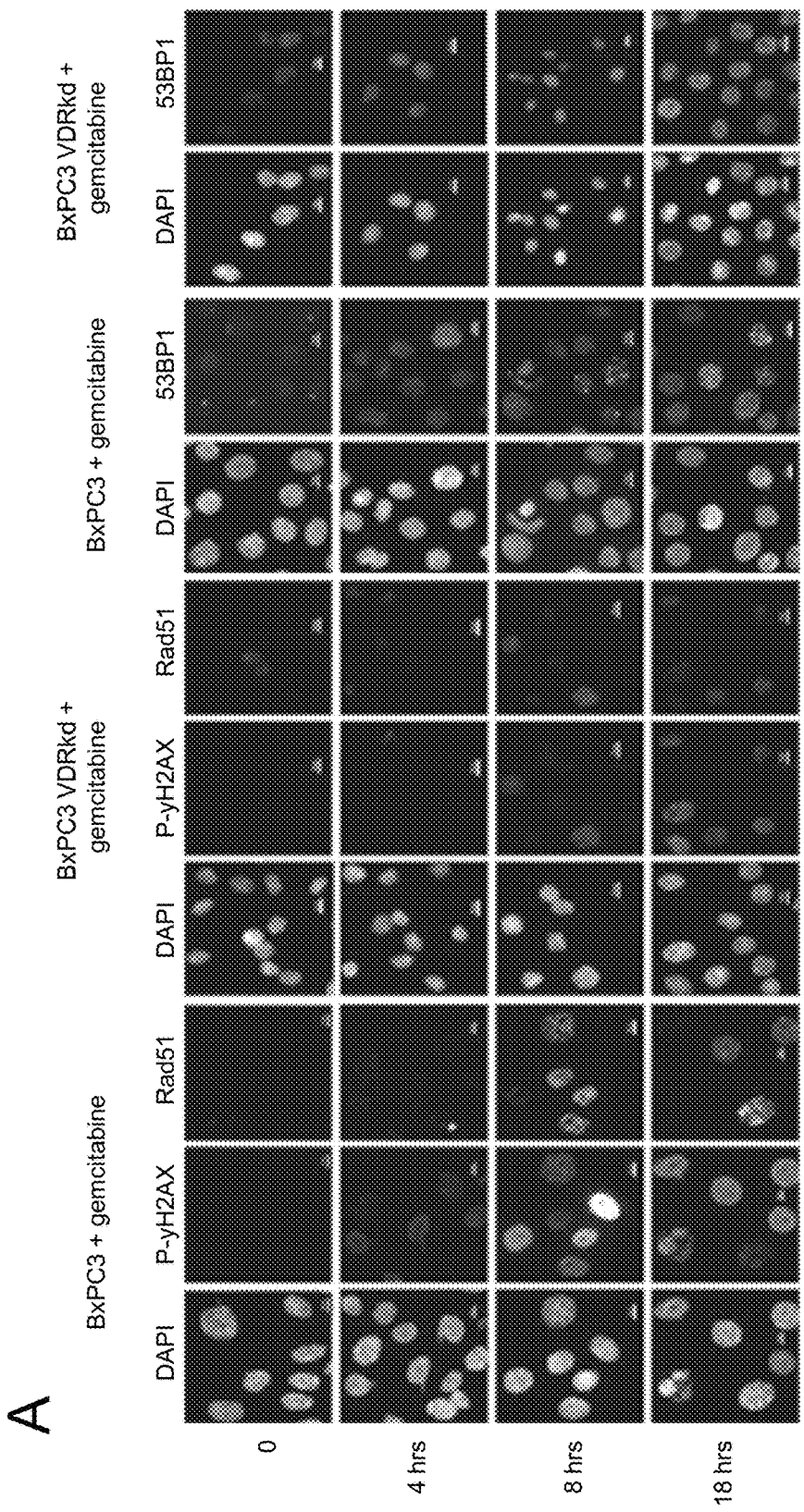
FIG. 3: VDR knockdown reduces gemcitabine induced γH2AX and Rad51 foci formation in BXPC3 and Panc1 cells. (A) Cells were treated with 50 nM gemcitabine, fixed at 0, 2 hrs, 3 hrs, 4 hrs, 6 hrs, 8 hrs, and 18 hrs and stained for Rad51, γH2AX, and 53BP1. Representative images (40×) from 0, 4, 8 and 18 hrs post drug treatments are shown. (B) Higher magnification (90×) confocal images of individual nuclei displaying the different staining patterns of Rad51, γH2AX, and 53BP1 after VDR knockdown compared to controls. Percentages of each pattern from 500 cells/sample analyzed are presented.
Figure 3:
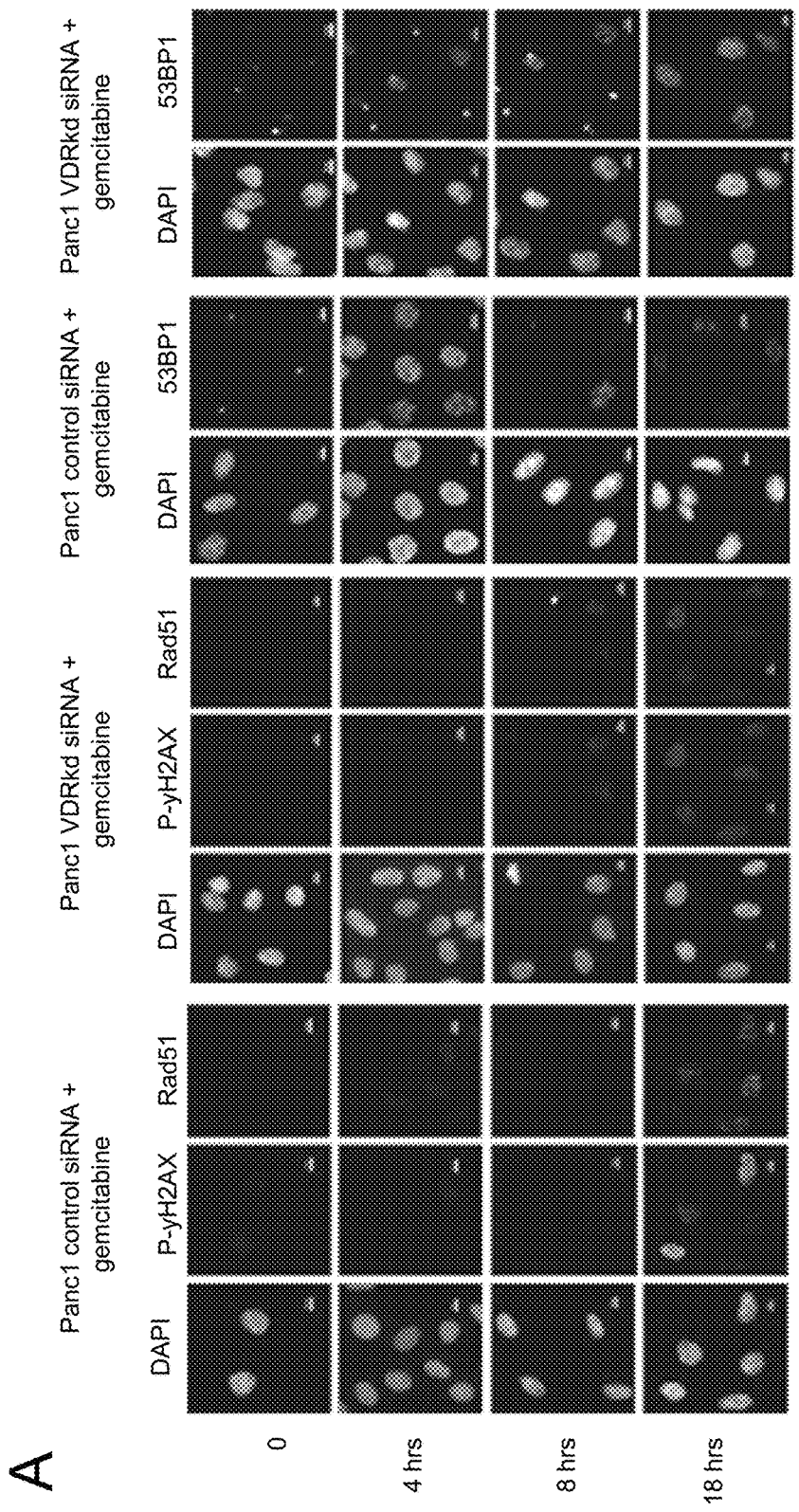
Figure 3:
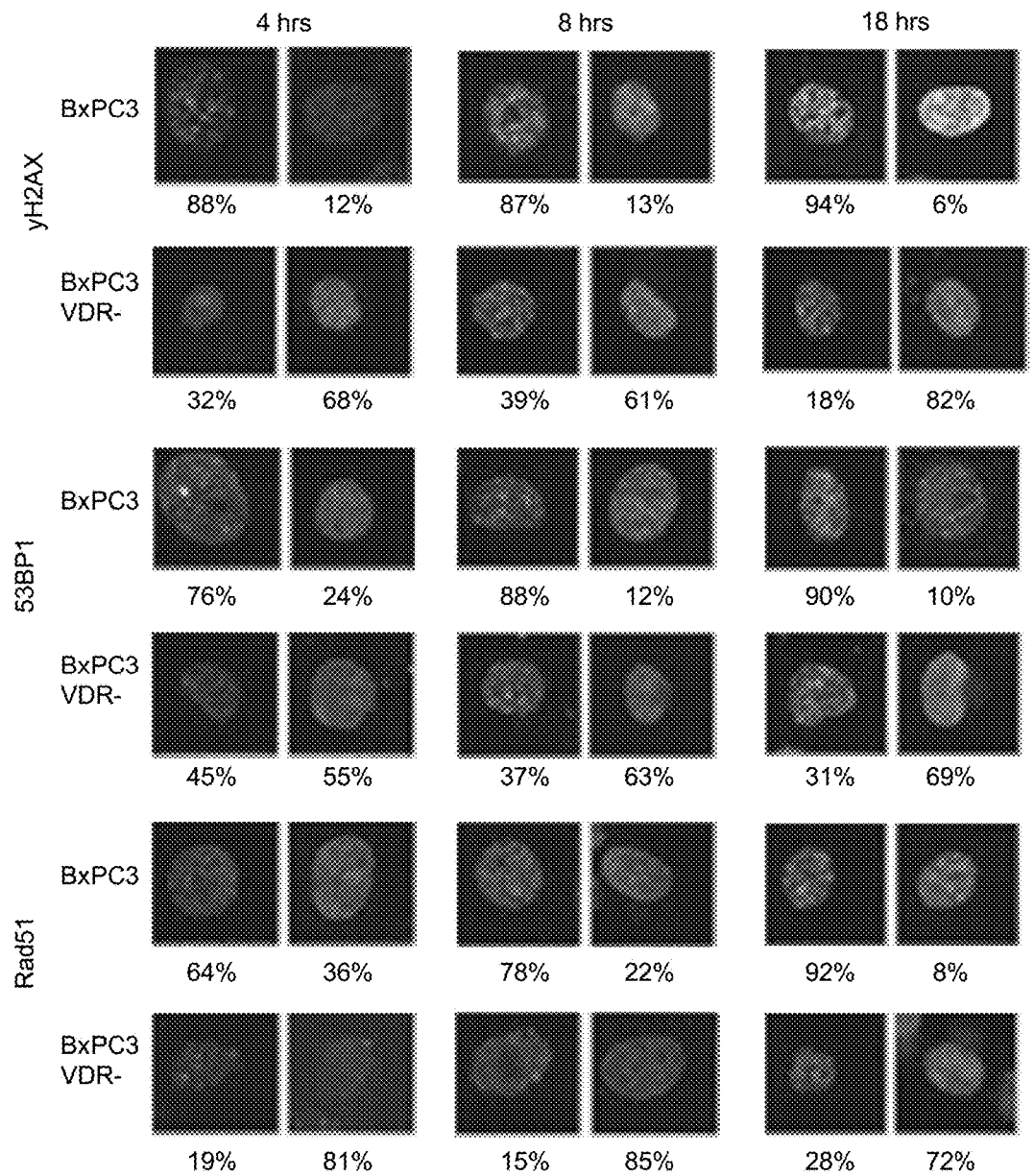
Figure 4:
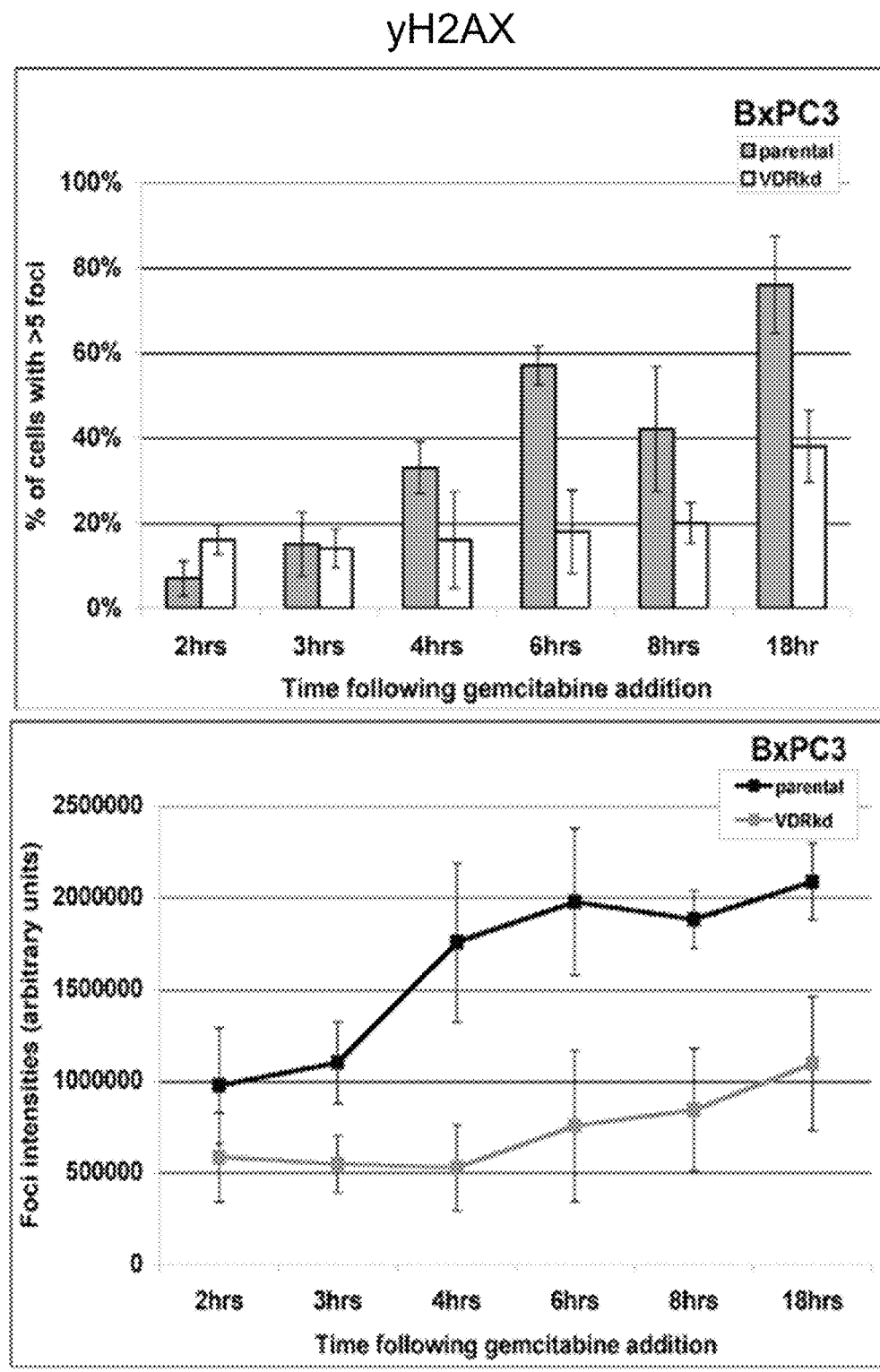
FIG. 4: Quantification of Rad51, γH2AX, and 53BP1 staining of BxPC3 cells. Individual nuclei from images in FIG. 3 were separately analyzed for foci number and focal intensity. Quantitation was performed on cells treated with gemcitabine for 0, 2 hrs, 3 hrs, 4 hrs, 6 hrs, 8 hrs, and 18 hrs. 500 cells from each timepoint was examined for Rad51, γH2AX, and 53BP1.
Figure 4:
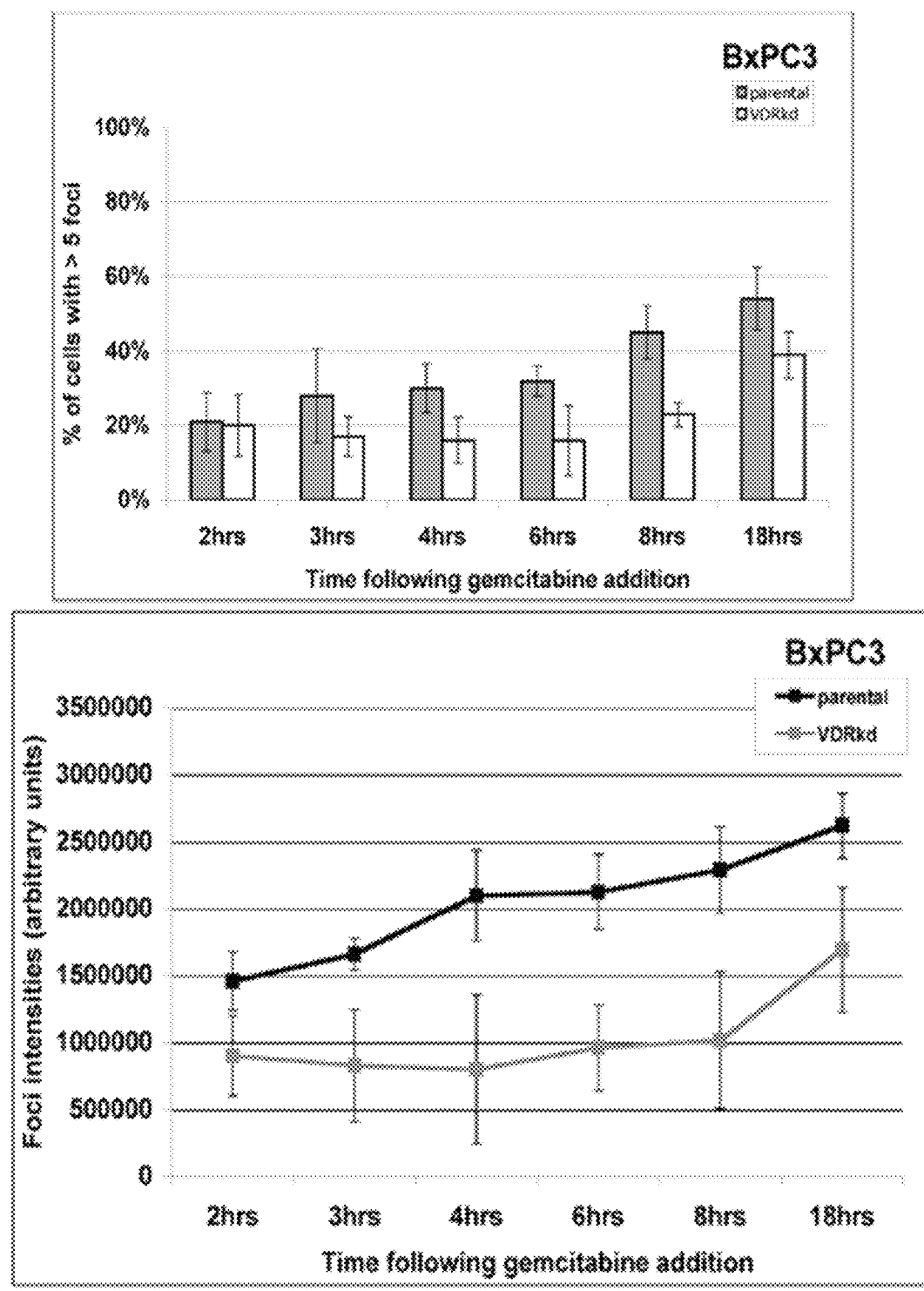
Figure 4:
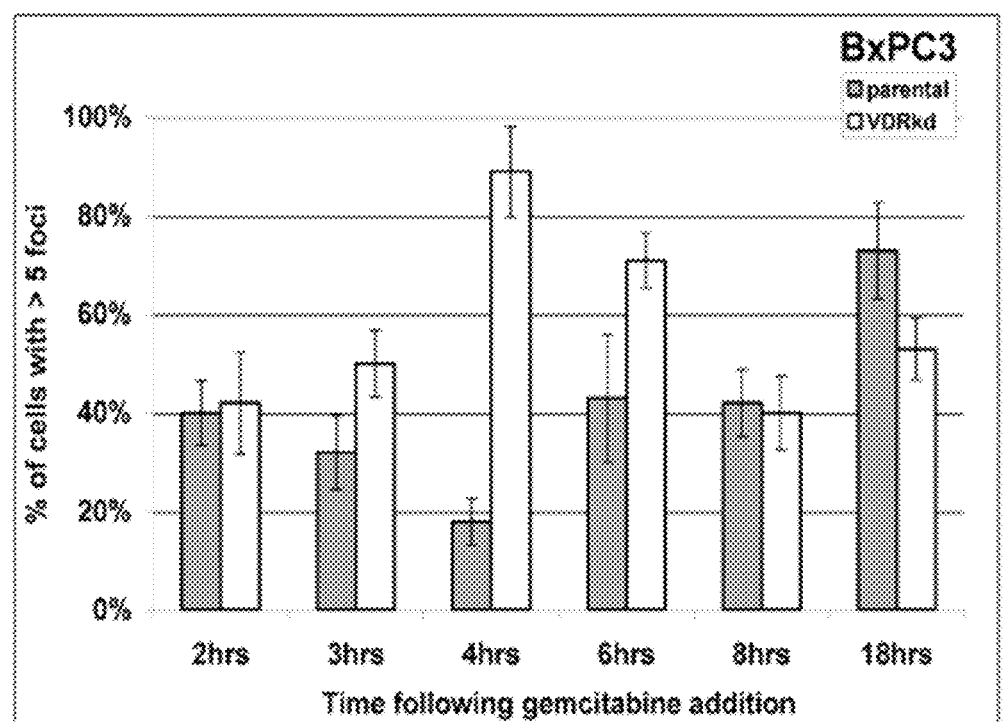
Figure 4:
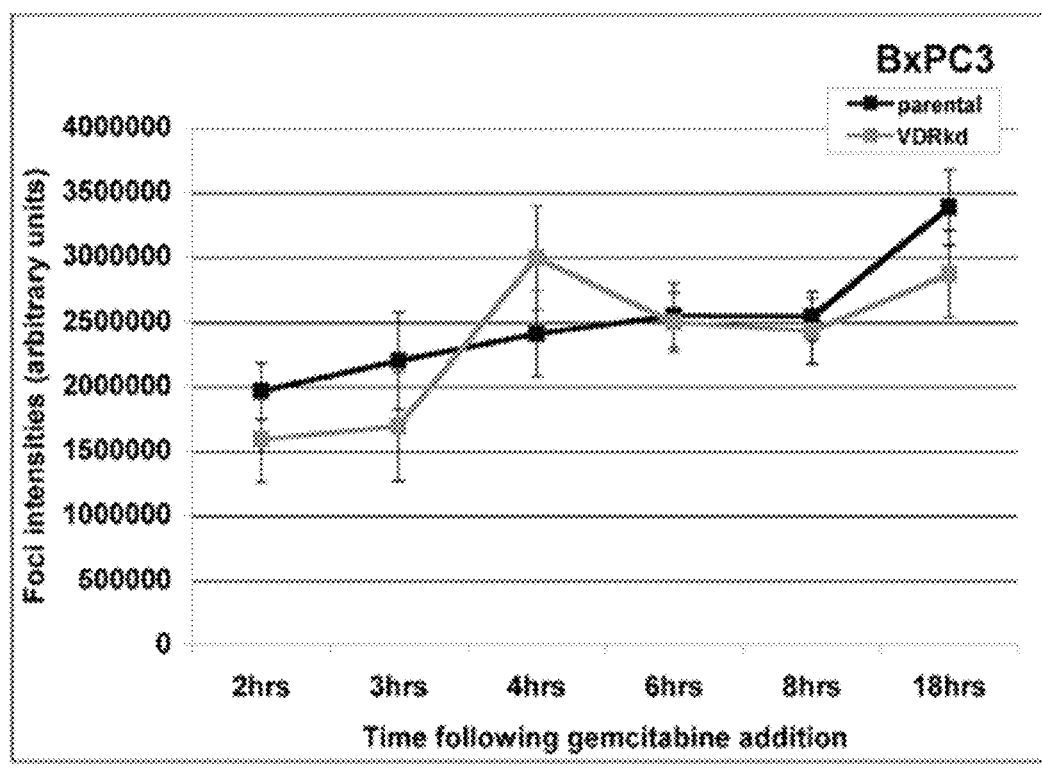
Figure 5:
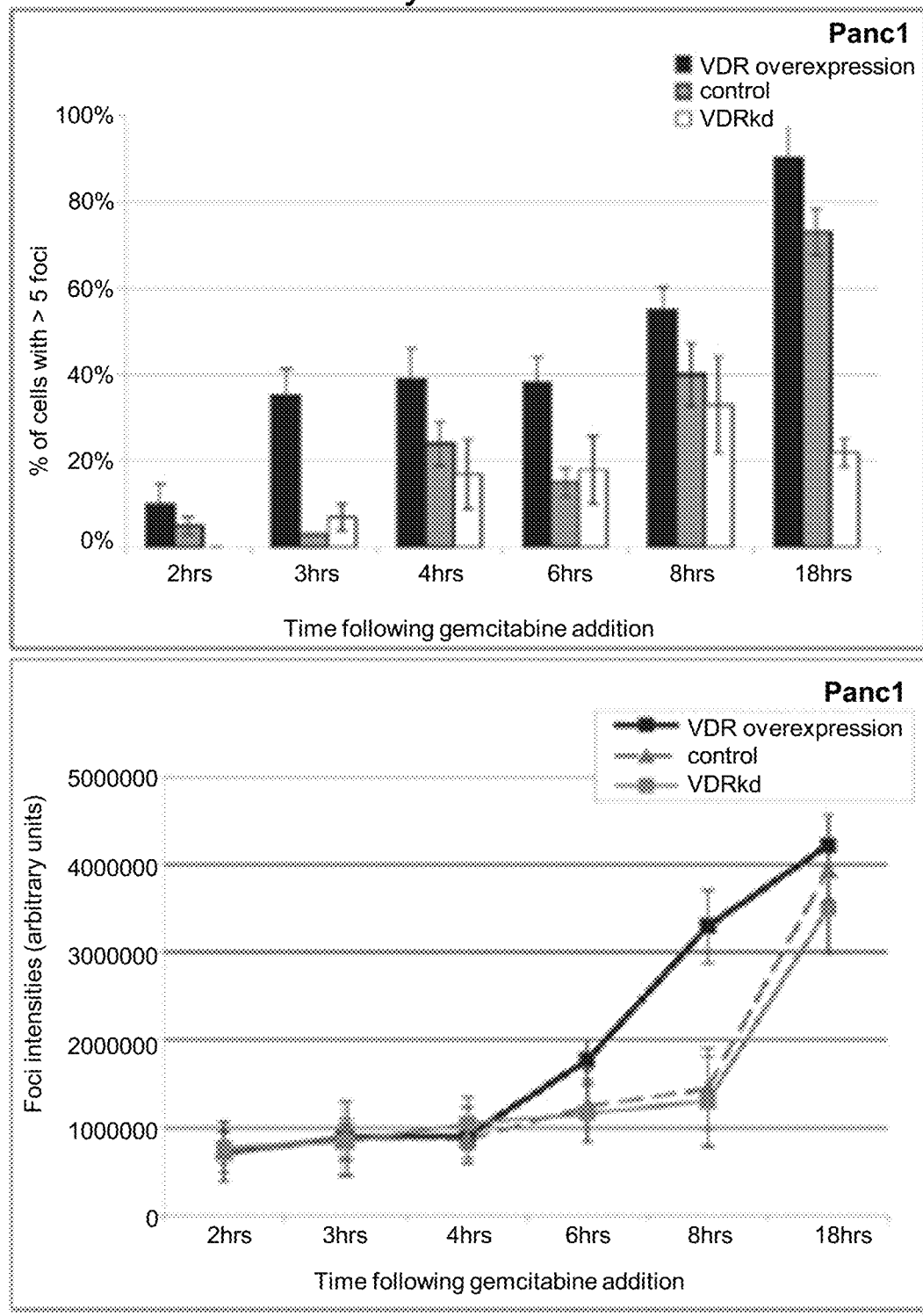
FIG. 5: Quantification of Rad51, γH2AX, and 53BP1 staining of Panc 1 cells. Individual nuclei from images in FIG. 3 were separately analyzed for foci number and focal intensity. Quantitation was performed on cells treated with gemcitabine for 0, 2 hrs, 3 hrs, 4 hrs, 6 hrs, 8 hrs, and 18 hrs. 500 cells from each timepoint was examined for Rad51, γH2AX, and 53BP1.
Figure 5:
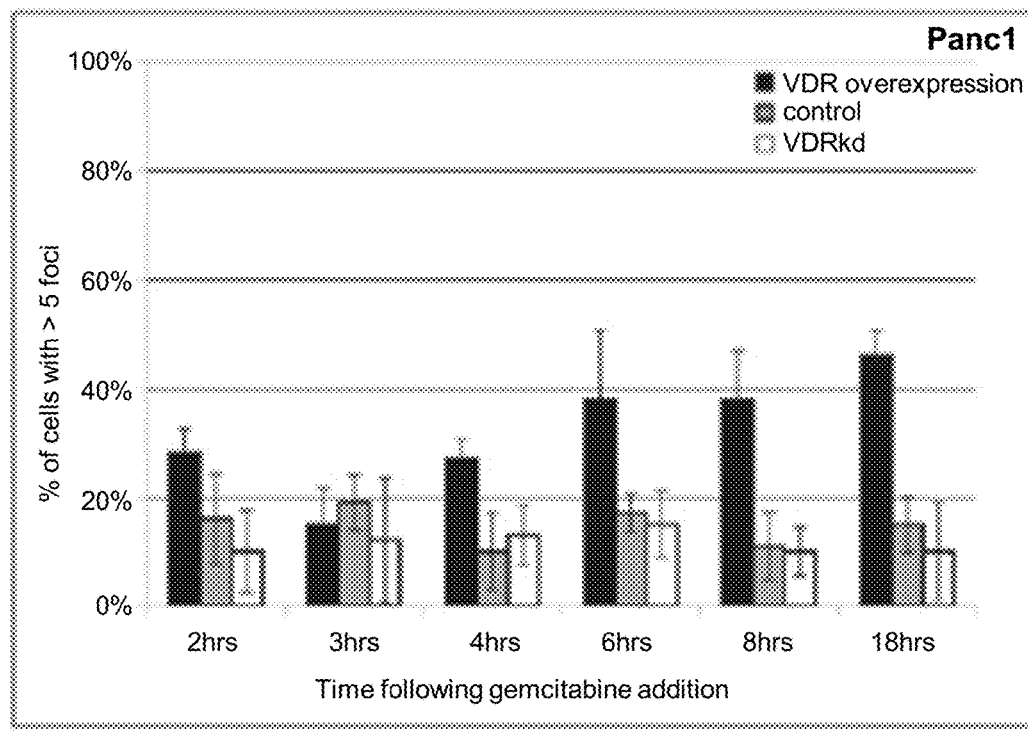
Figure 5:
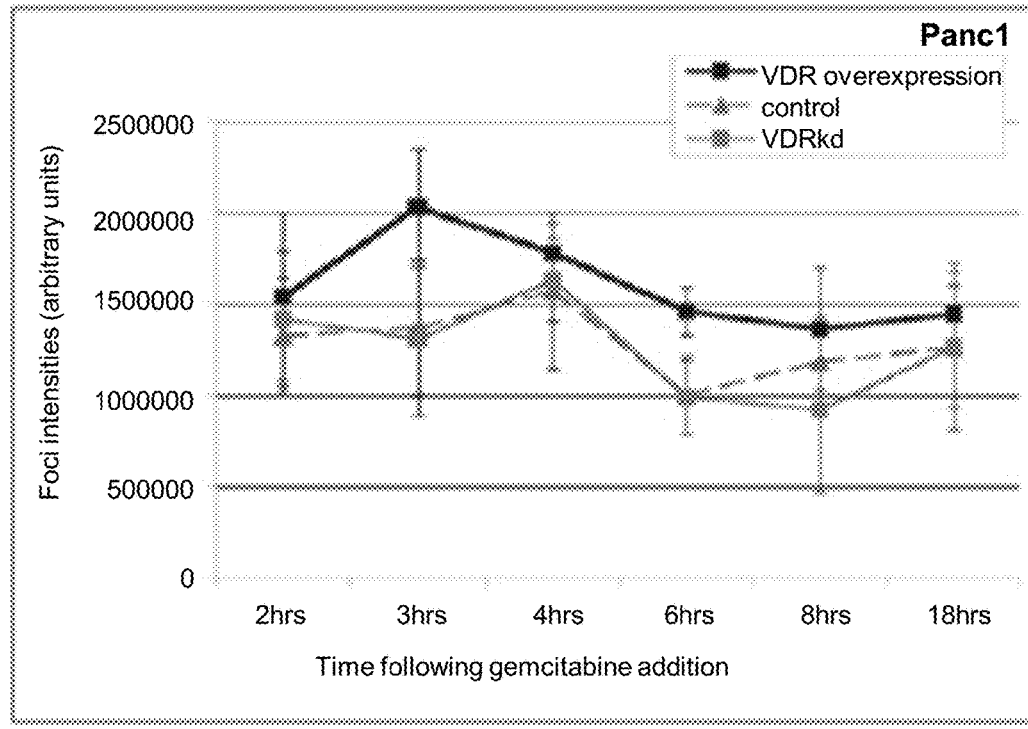
Figure 5:
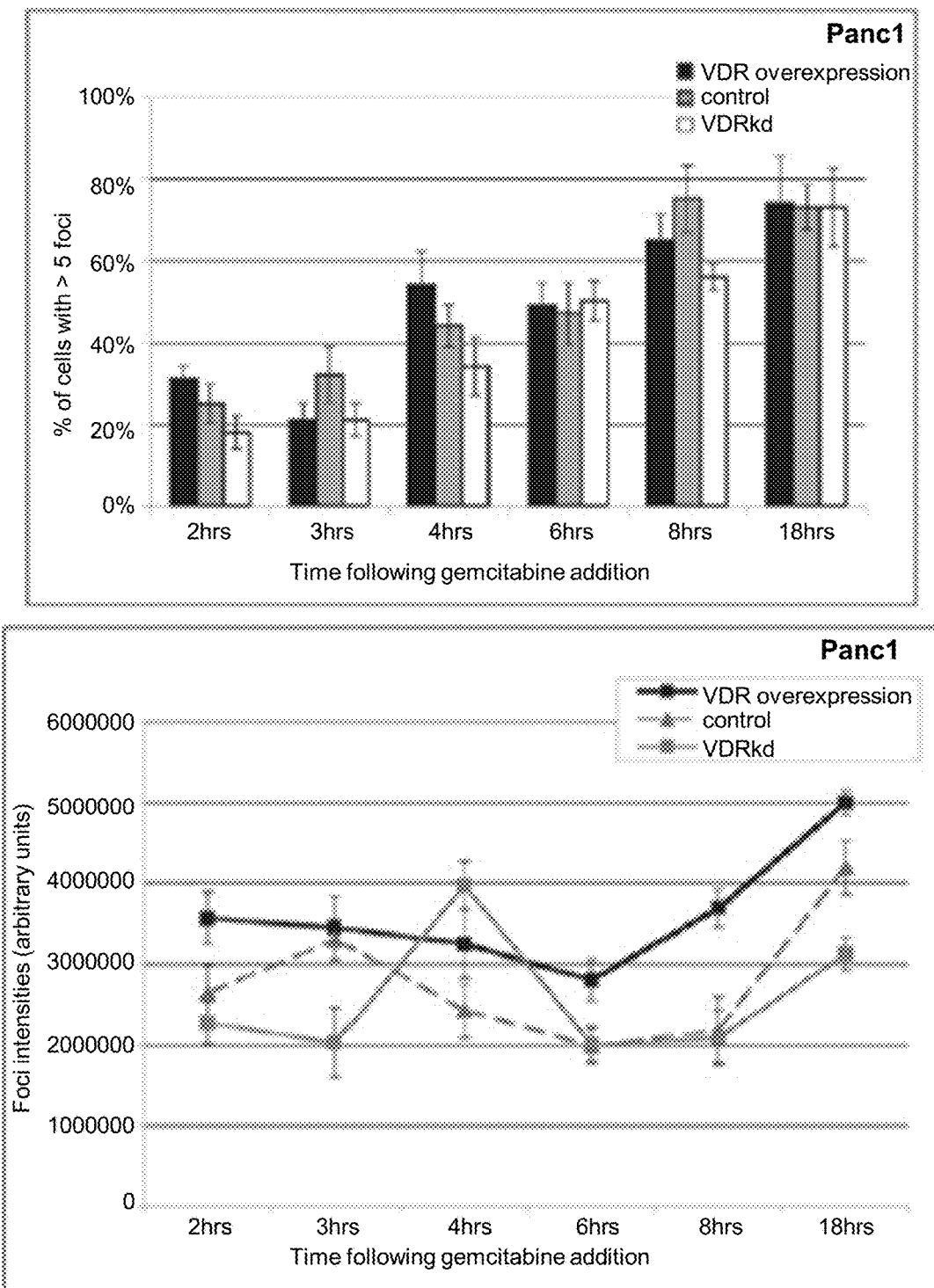

It was investigated if these repair pathways were abrogated after VDR knockdown by staining for foci formation by phospho-γH2AX, Rad51, and 53BP1, and measuring intensities after gemcitabine treatment (FIGS. 3, 4, and 5). BxPC3 (high VDR expression) and Panc1 (low VDR expression) cells were treated with gemcitabine (50 nM) for 2, 4, 8, and 18 hours, and fixed and stained for phospho-γH2AX, 53BP1, and Rad51. Foci quantitation included counting of nuclei with >5 foci and a separate measurement of the sum intensities of foci that were averaged for 5 separate immunofluorescence experiments. Thus, the foci counts do not reflect their intensities, which were quantitated separately. Weak but detectable phospho-γH2AX foci were visible within 4 hours of gemcitabine treatment in BxPC3 cells while it took 18 hours for foci to form in Panc1 cells (FIG. 3, A). Similarly, Rad51 foci were visible after 8 hours of gemcitabine treatment in BxPC3 cells compared to 18 hours in Panc1 cells (FIG. 3, A, FIG. 4, and FIG. 5). The kinetics of 53BP1 foci formation were comparable between the two cell lines.

Next, it was investigated whether VDR deficiency affected the kinetics of foci formation in BxPC3 and Panc1 cells. The kinetics of foci formation in the BxPC3 VDRkd cells were compared to the foci formation observed in the parental cells. Transient siRNA transfections were used to knockdown VDR in the Panc1 cells. VDR knockdown delayed foci formation and reduced foci intensities of phospho-γH2AX and Rad51 in both cell lines (FIG. 3, A, FIG. 4, and FIG. 5). 53BP1 foci formation kinetics did not seem to be affected by VDR knockdown in either cell line (FIG. 3, A, FIG. 4, and FIG. 5). Phospho-γH2AX and Rad51 foci in BxPC3 VDRkd cells were detected 8 and 18 hours, respectively, following addition of gemcitabine as compared to 4 and 8 hours, respectively, in the parental cells. Similarly, Panc1 cells transfected with VDR siRNA did not exhibit phospho-γH2AX and Rad51 foci until 18 hours following gemcitabine addition as compared to ~8 hours for Panc1 cells transfected with control. The slower kinetics of foci formation in Panc1 cells was accelerated by transient VDR overexpression in Panc1 cells (FIG. 5).

Along with the delayed kinetics foci formation and reduced intensities of phospho-7H2AX and Rad51 after VDR knockdown, qualitative differences were observed in the staining patterns of Rad51, 53BP1, and phospho-γH2AX. Parental BxPC3 cells form discrete punctate phospho-γH2AX foci compared to the VDRkd cells that displayed a diffuse, pan nuclear phospho-γH2AX staining pattern (FIG. 3, B). The punctate pattern is indicative of damage recognition and subsequent repair complex formation near the sites of damage. In contrast, the diffuse pattern is indicative of damage recognition, but is believed to reflect a failure to retain repair complexes distal to damage sites which leads to further accumulation of DNA damage that eventually leads to catastrophic cell death.

Phospho-γH2AX formed punctate foci 18 hours after gemcitabine treatment in 94% of the parental BxPC3 cells. By contrast, punctate foci were seen in only 18% of the VDRkd cells and the remaining 82% of the cells exhibited a diffuse pattern (FIG. 3, B). Although the kinetics of foci formation by 53BP1 was not affected by VDR knockdown (FIG. 3, A), it also exhibited a more diffuse 53BP1 staining pattern as seen for phospho-γH2AX (FIG. 3B). After 18 hours of gemcitabine treatment, 90% of the parental cells formed punctate 53BP1 foci and 10% expressed the diffuse pattern. This contrasts with only 31% of the VDRkd cells formed punctate foci while 69% expressed the diffuse pattern.

Similarly, Rad51 foci formation was also compromised in the VDRkd cells. After 18 hours of gemcitabine treatment, 92% of the parental BxPC3 cells exhibited clear Rad51 foci as compared to 28% of the VDRkd cells. 72% of VDRkd cells (which were also phospho-γH2AX positive) exhibited diffuse Rad51 staining as compared to only 8% that were seen in the parental cells (FIG. 3, B). Therefore, VDR knockdown not only delays the kinetics of foci formation of phospho-γH2AX and Rad51, but also compromises the ability of phospho-γH2AX, 53BP1, and Rad51 to form punctate foci.

The reduction in Rad51 foci formation in gemcitabine treated cells depleted of VDR suggested an impairment in HR. To functionally test whether HR has been compromised after VDR knockdown, the sensitivity of parental and VDR knockdown cells to the PARP inhibitor Rucaparib was compared. This is based on the observation that PARP inhibitors selectively kill BRCA1 defective cells because of their HR deficiency. Furthermore, PARP inhibition has been shown to increase Rad51 foci, and depletion of Rad51 sensitized cells to PARP inhibition.

BxPC3 and Panc1 cells were transfected with control, VDR, and BRCA1 siRNAs and their sensitivity to Rucaparib treatment was compared by clonogenic survival. The results clearly showed that VDR knockdown rendered both cell lines more sensitive to Rucaparib than the controls. For BXPC3 cells, the $IC_{50}$s after knockdown of BRCA1 and VDR were 1 and 5 uM, respectively (FIG. 6, A) compared to the control IC50 of 9 μM. For Panc1 cells, the $IC_{50}$s after knockdown of BRCA1 and VDR were 3.5 and 400 nM, respectively (FIG. 4, A) compared to the control ($IC_{50}$=4 μM). The difference in sensitivities to Rucaparib between VDR and BRCA1 knockdown was due to the fact that Rad51 foci formation was more efficiently inhibited in BRCA1 depleted cells. The increased sensitivity of cells depleted of VDR to Rucaparib supports the data that suggests Rad51 mediated HR functions are impaired.

Figure 6:
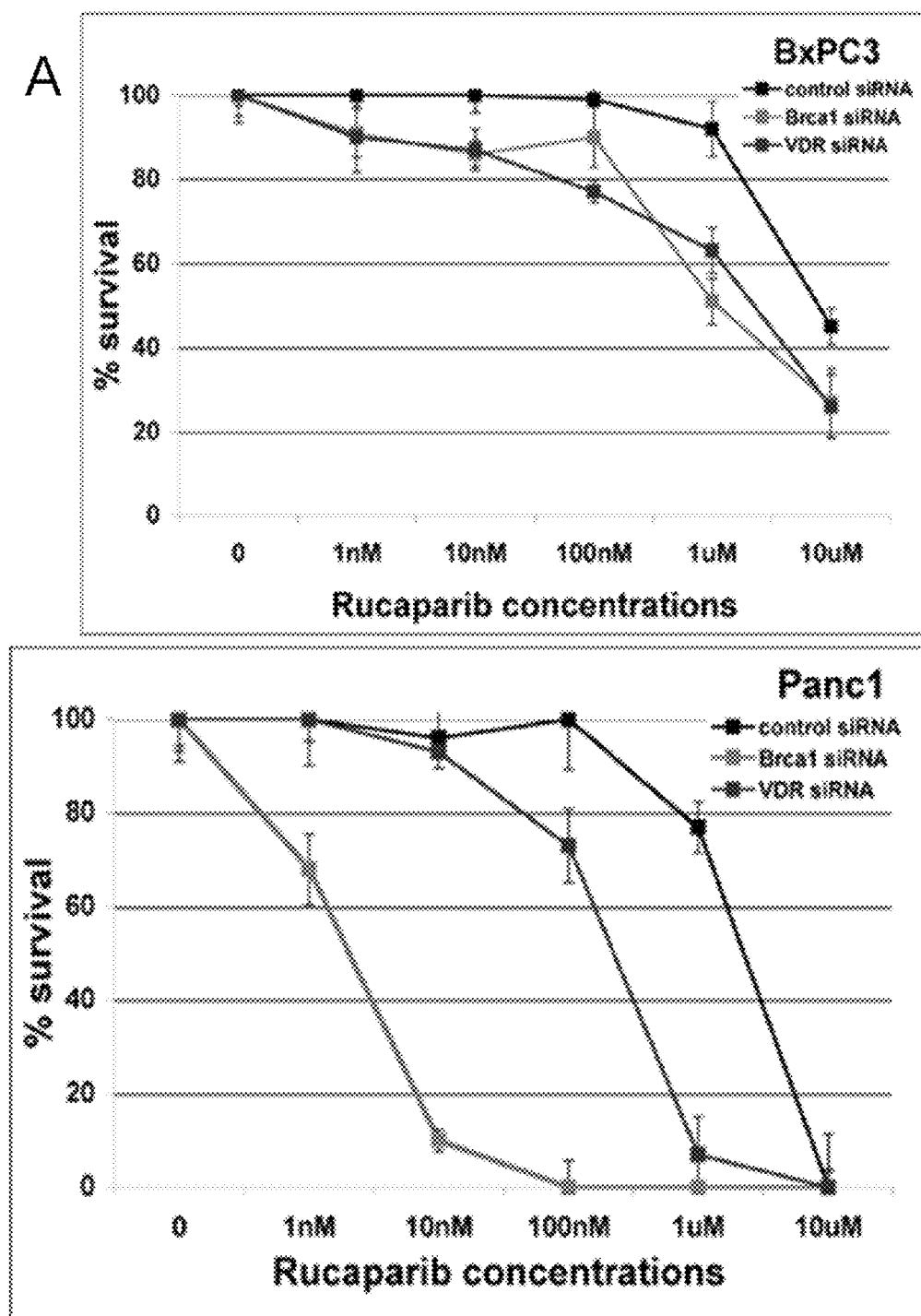
FIG. 6: VDR knockdown sensitizes BXPC3 and Panc1 cells to the PARP inhibitor, Rucaparib, blocks gemcitabine induced DSB HR repair by reducing Rad51 foci formation at DSBs. (A) Rucaparib kill curves generated from clonogenic assays of cells transfected with control, BRCA1 and VDR siRNAs. (B) Western blot comparing Rad51 and γH2AX protein levels of BxPC3 and BxPC3 VDRkd cells. 40 μg of protein loaded. Lane 1=BxPC3+vehicle (18 hrs) (supernatant fraction); Lane 2=BxPC3+gemcitabine (50 nM) (18 hrs) (supernatant fraction); Lane 3=BxPC3 VDRkd+vehicle (18 hrs) (supernatant fraction); Lane 4=BxPC3 VDRkd+gemcitabine (50 nM) (18 hrs) (supernatant fraction); Lane 5=BxPC3+vehicle (18 hrs) (pellet fraction); Lane 6=BxPC3+gemcitabine (50 nM) (18 hrs) (pellet fraction); Lane 7=BxPC3 VDRkd+vehicle (18 hrs) (pellet fraction); Lane 8=BxPC3 VDRkd+gemcitabine (50 nM) (18 hrs) (pellet fraction). (C) Comparison of Rad51 and γH2AX staining of BxPC3 and BxPC3kd cells following TSA (500 nM)+gemcitabine (50 nM) treatments. (D) Colony survival of BxPC3 VDRkd and BxPC3 parental cells treated with TSA (500 nM)+gemcitabine (n=3). P values: BxPC3 VDRkd=0.289, BxPC3 control=0.02.
Figure 6:
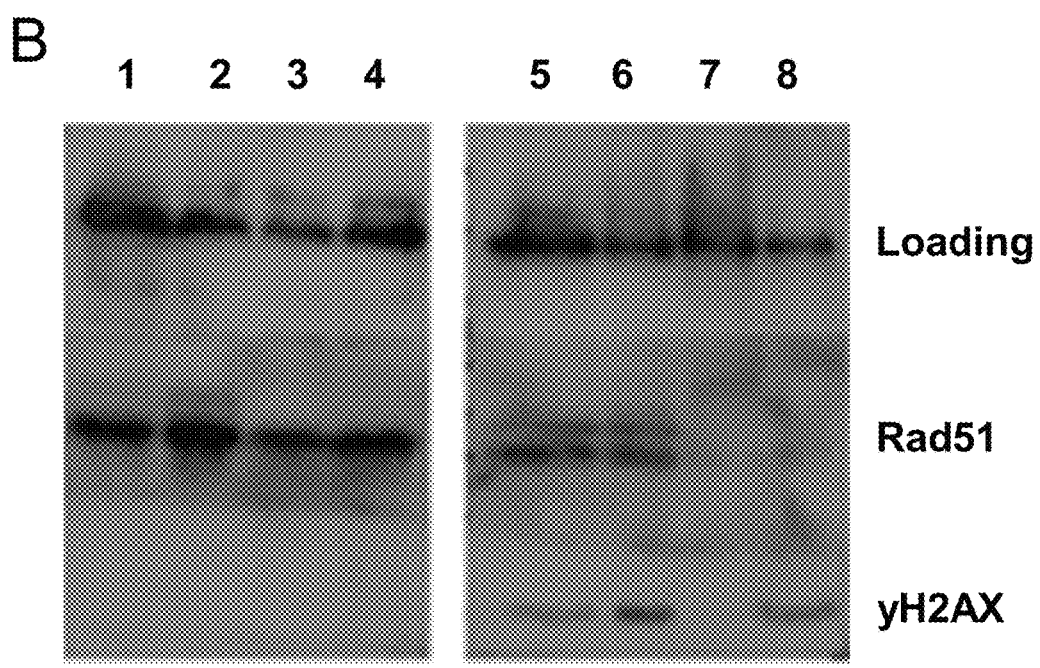
Figure 6:
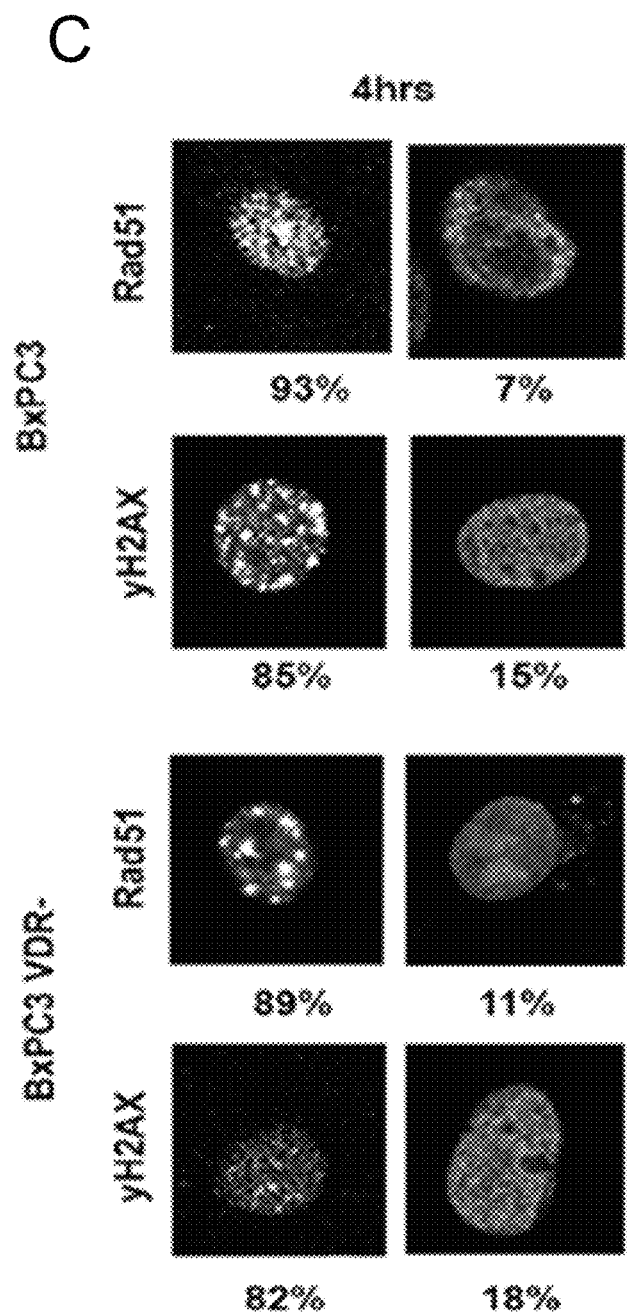
Figure 6:
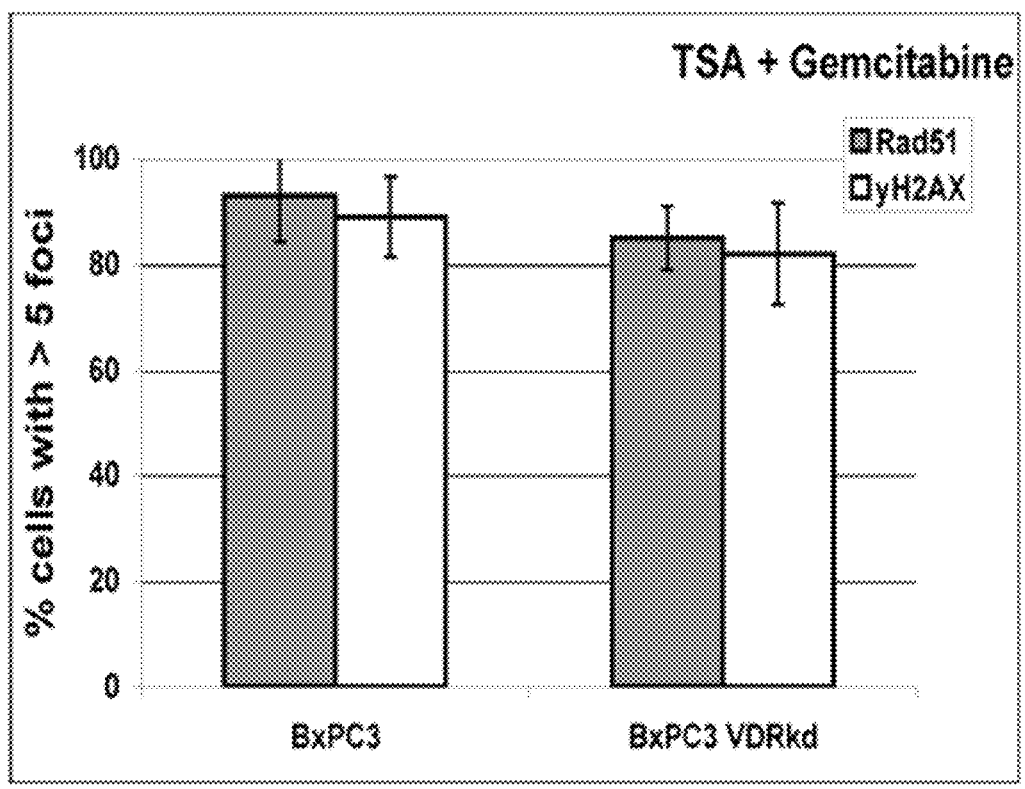
Figure 6:
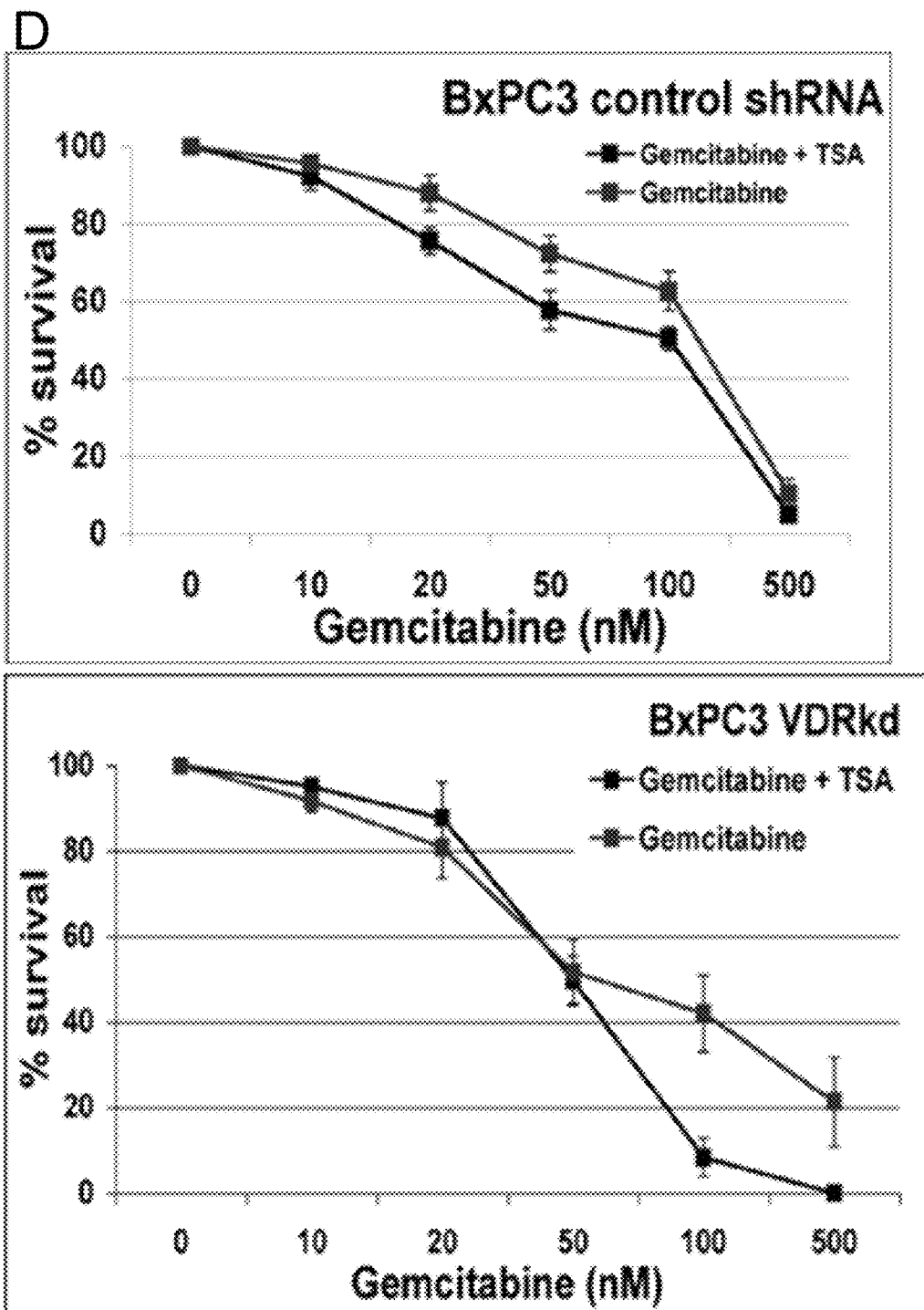

As VDR is a transcription factor, it may regulate the expression of DNA repair genes such as Rad51 and γH2AX. Comparison of the levels of these two proteins between parental and after VDR knockdown did not show a significant difference that would account for the reduced ability to form DNA damage foci induced by gemcitabine. Western blots were performed to assay VDR's role in regulating the expression of γH2AX, 53BP1, and Rad51 after DNA damage induction. Parental and BxPC3 VDRkd cells treated with gemcitabine for 18 hours expressed equivalent amounts of Rad51 and H2AX in whole cell extracts (supernatants) (FIG. 6, B). However, analysis of the chromatin fractions showed very low amounts of Rad51 and phospho-γH2AX in VDRkd cells compared to the parental BxPC3 cells (FIG. 6, B). This supported the staining data that Rad51 and phospho-γH2AX foci formation were impaired in VDR depleted cells treated with gemcitabine. To further examine if VDR might be regulating the expression of these and other DNA damage response genes, RNAseq was used to compare the transcriptomes of BXPC3 parental and VDRkd cells of Rad51 and H2AX. This analysis did not identify significant differences in their mRNA levels though the transcript numbers were slightly (<2 fold) reduced in the BxPC3 VDRkd cells compared to the parental BxPC3 cells.

Rad51 foci formation has been shown to depend on histone acetylation. The histone acetyltransferases TIP48, 49, and 60 have been shown to modulate Rad51 foci formation in response to DNA damage through histone acetylation. Given that VDR forms complexes with coactivators that contain historic acetylases and corepressors that contain HDACs, it may use this activity to specify Rad51 foci formation. VDRkd cells were treated with the HDAC inhibitor, Trichostain A (TSA) (500 nM), and Rad51 foci formation after gemcitabine treatment (50 nM) were monitored (FIG. 6, C). In the absence of TSA, 11% of the VDRkd cells exhibited Rad51 foci after 4 hrs in gemcitabine as compared to 89% positive cells after TSA treatment. This increase was comparable to parental cells where 92% of the cells exhibited Rad51 foci within 4 hours of gemcitabine treatment.

To test the functional relevance of the TSA mediated Rad51 foci formation in the VDR knockdown cells, whether TSA altered the sensitivity to gemcitabine was investigated. Using the same concentration of TSA (500 nM) that restored the kinetics of Rad51 foci formation, it did not render the VDRkd cells more sensitive to gemcitabine than cells without TSA treatment (both treatments had an $IC_{50}$ of 50 nM of gemcitabine) (FIG. 6, D). Parental cell sensitivity to gemcitabine was increased by TSA treatments at the concentrations tested (p=0.02). The $IC_{50}$ for the gemcitabine plus TSA treated cells was 100 nM compared to cells treated with gemcitabine alone which had an $IC_{50}$ of ~200 nM (FIG. 6, D).

Figure 7:
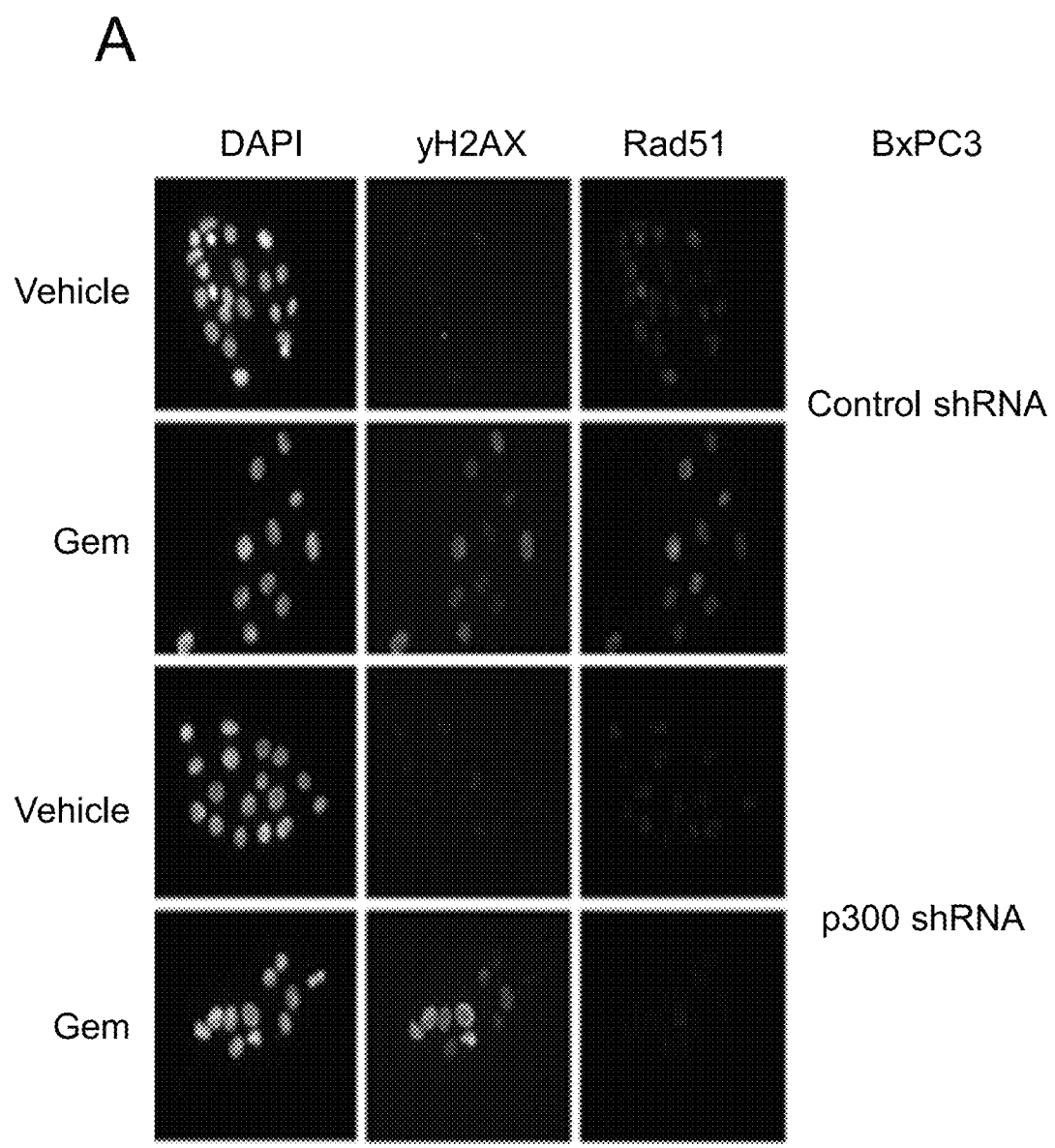
FIG. 7: p300 knockdown reduces gemcitabine induced Rad51 foci formation. (A) Rad51 and γH2AX staining of BxPC3 or Panc1 cells treated with control and p300 shRNA's, and treated with vehicle or gemcitabine, (B) Clonogenic survival assay of BxPC3 and Panc1 cells transfected with p300 shRNA and treated with different doses of gemcitabine=3). p values: BxPC3=0.0489, Panc1=0.192.
Figure 7:
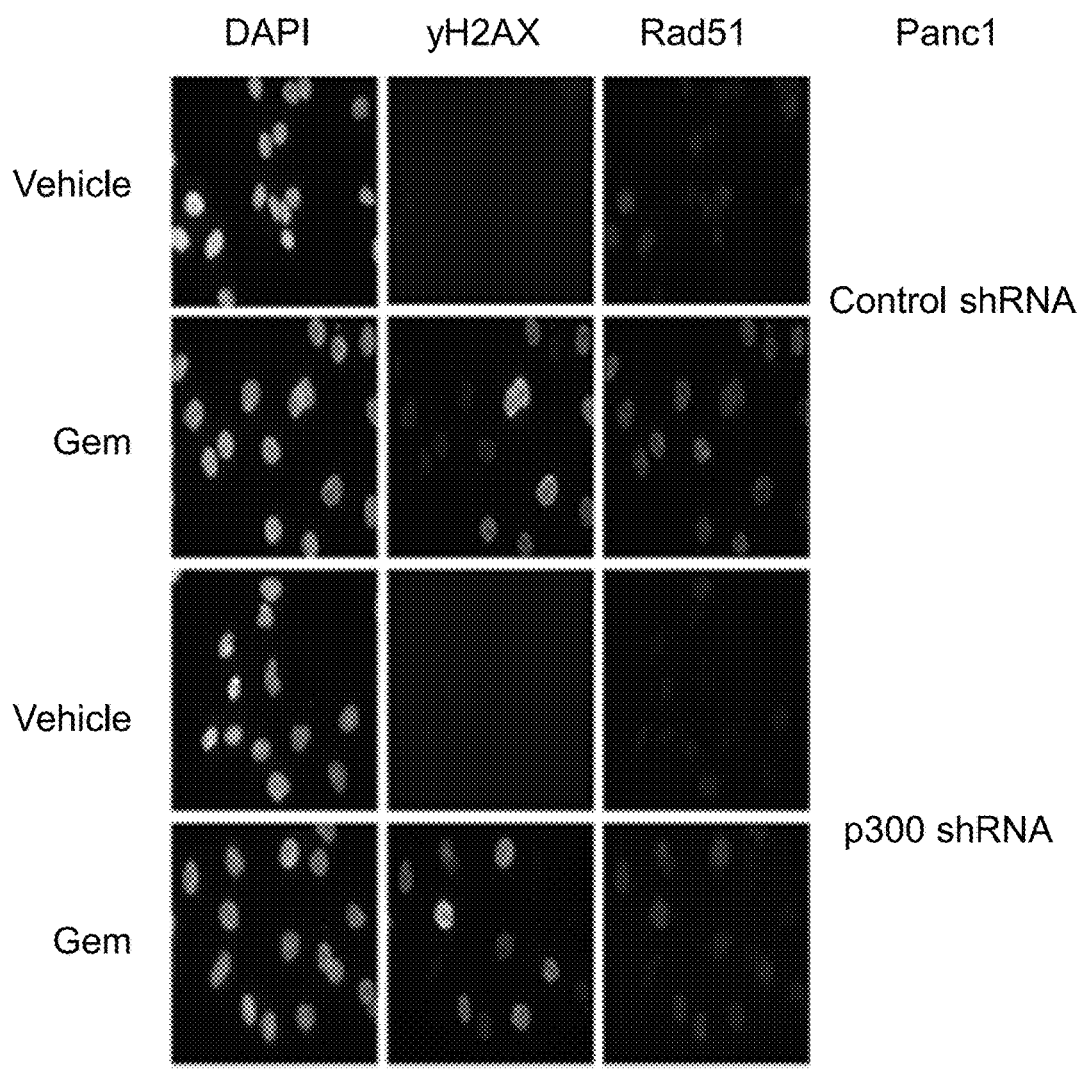
Figure 7:
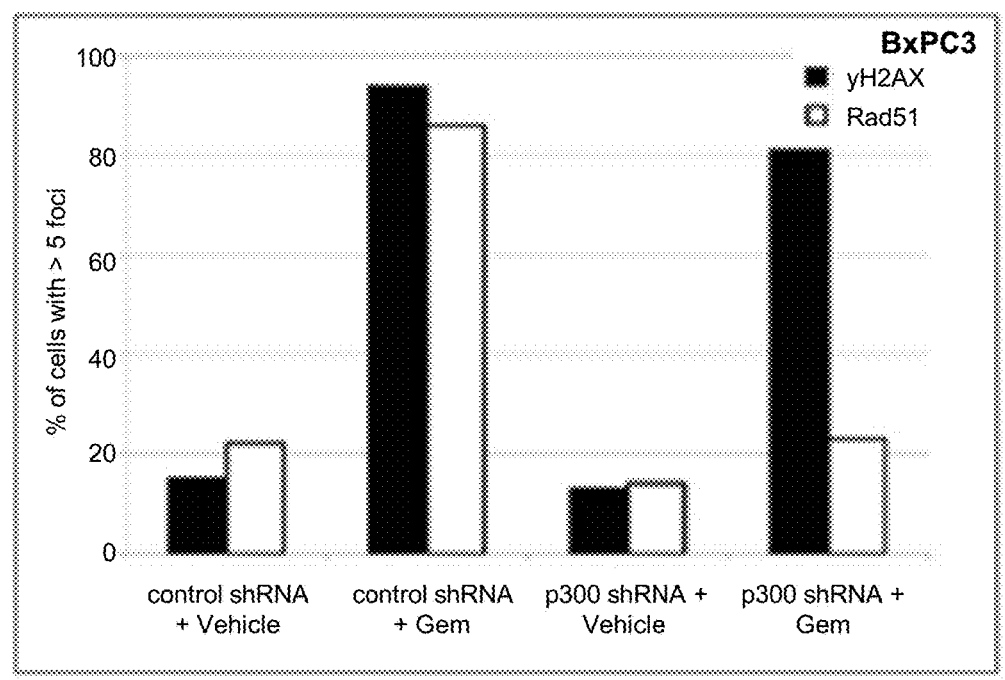
Figure 7:
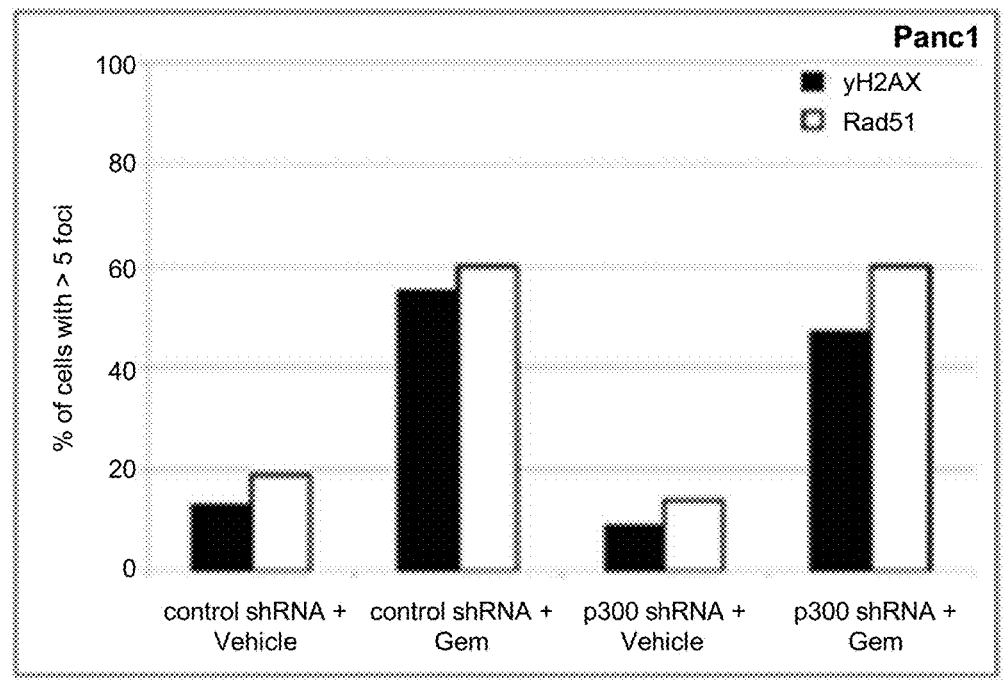
Figure 7:
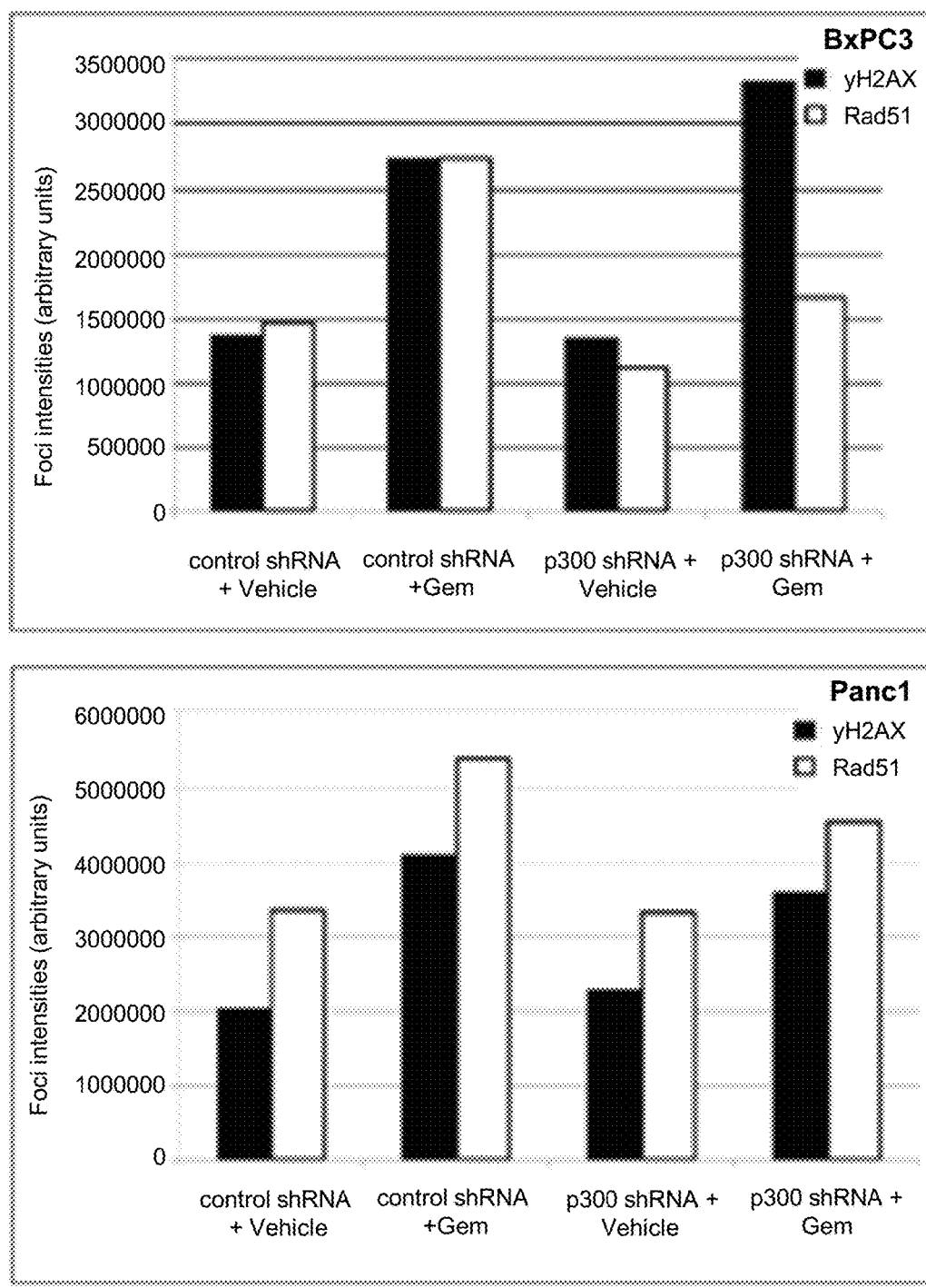
Figure 7:
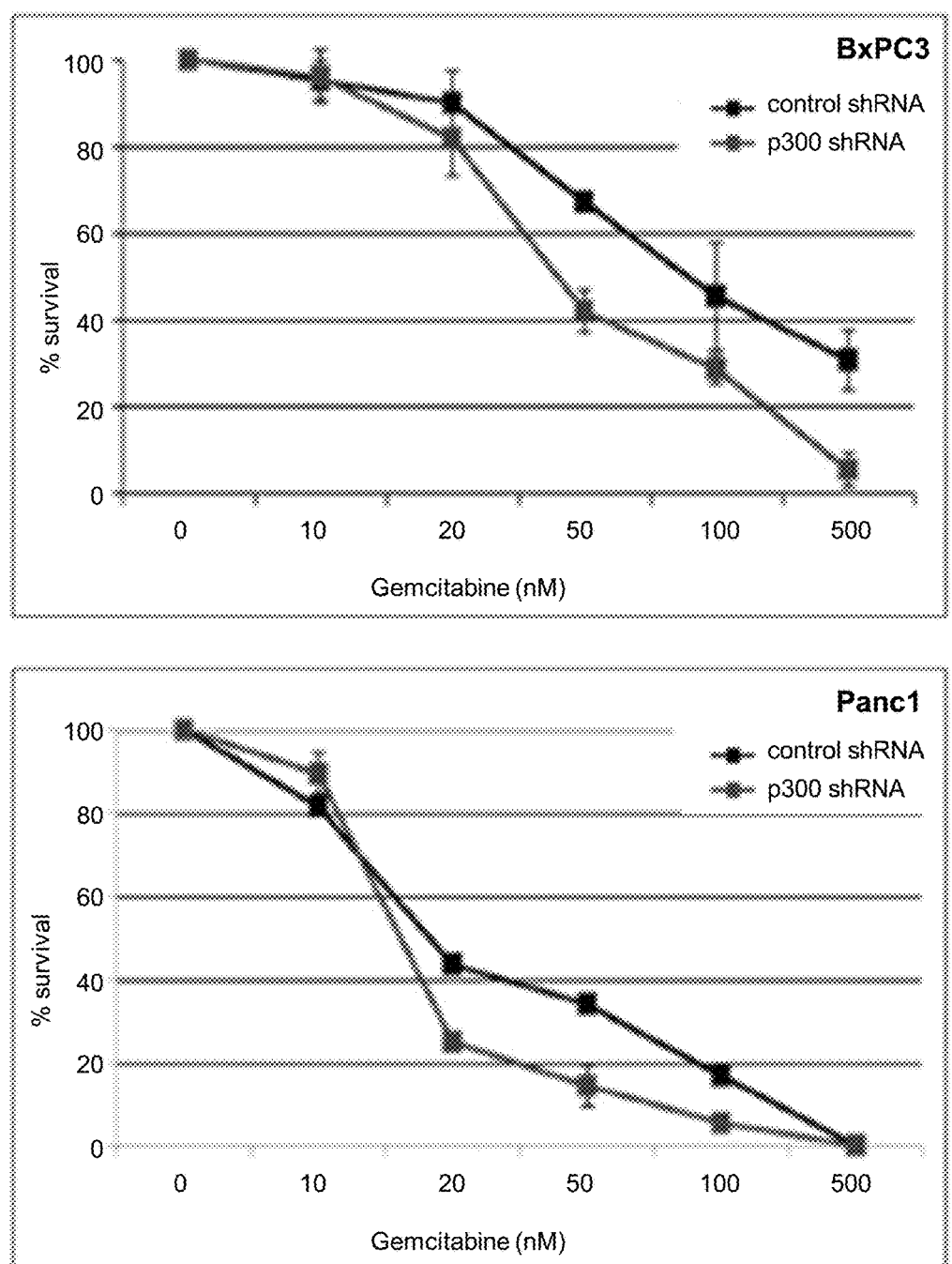

The contribution of the p300 HAT (histone acetyltransferase) in Rad51 foci formation was tested because p300 interacts with VDR to activate transcription of specific target genes. p300 also has been shown to directly promote Rad51 transcription following DSB induction in lung cancer cell lines. First, p300 was depleted from BxPC3 and Panc1 cells using shRNAs, and cells were treated with gemcitabine and Rad51 foci formation were monitored over time. The number of Rad51 foci and overall intensity was reduced in the p300 shRNA transfected cells compared to control cells (FIG. 7A). Of the BxPC3 cells transfected with p300 shRNA, ~22% were positive for Rad51 foci (>5 foci/nucleus) compared to ~84% of the control cells 18 hrs post gemcitabine treatment. Overall, Rad51 focal intensity was also reduced by ~35% in the p300 knockdown cells compared to control cells. Gemcitabine sensitivity was also tested after p300 knockdown (FIG. 7, B). Consistent with the decreased Rad51 foci, p300 knockdown effectively sensitized BxPC3 cells to gemcitabine. The control shRNA treated cells had an $IC_{50}$ of ~80 nM while the p300 shRNA treated cells had an $IC_{50}$ of ~40 nM (p=0.0489). Panc1 cells also did not exhibit increased sensitivity to gemcitabine following p300 knockdown with the $IC_{50}$s of p300 knockdown cells and control cells being similar at ~16 nM and ~19 nM, respectively.

Example 6

Summary

Twenty seven target genes that contributed to gemcitabine survival in Panc1 cells were identified. Analysis by STRING and Ingenuity identified two networks that specified gemcitabine survival. One was the DNA damage response network that consisted of CHK1, Wee1, PIAS4, and 53BP1. These genes validated the screen. VDR was part of a second network that also included SRF, and MMP13, Runx2, a VDR binding partner and transcription factor, activates the MMP13 gene during prostate cancer invasion and metastasis. Similarly, RXR-alpha, a major VDR binding partner, directly interacts with SRF and has been shown to compete with SRF for other binding partners like SRC-1 and p300. An acetylcholinesterase (ACHE), a dehydrogenase (BCK-DHB), phosphatases (DUSP23 and EPM2A), a transferase (GSTM3), a member of the pyruvate dehydrogenase complex (PDHA1), serine/threonine kinase (STK39), a cysteine peptidase (APG4D), a transporter (TNPO2), and transcriptional regulators (TBX4, TBX5, and KLF10) were identified.

It is believed that the VDR is a novel target for gemcitabine sensitization, and its knockdown enhanced gemcitabine killing as effectively as with Chk1 knockdown. However, the mechanism of sensitization is not via checkpoint override but rather to a previously unknown role of VDR in Rad51 mediated DNA repair. The data showed that VDR is required for the recruitment of Rad51, a key protein in error-free homologous recombination (HR) and is a determinant of gemcitabine sensitivity because of its role in repairing stalled replication forks.

The levels of VDR varied amongst Panc1, BXPC3 and CFPAC cells, and cells with higher levels were more resistant to gemcitabine. For all the cell lines, knockdown of VDR increased their sensitivity to gemcitabine. BXPC3 cells, which were most resistant to gemcitabine ($IC_{50}$ ~200 nM), showed the greatest reduction (~3-fold) in $IC_{50}$ after depletion of VDR. Transfection of wild type VDR into the VDR depleted BXPC3 cells increased the $IC_{50}$ ~6-fold over vector controls, and to levels seen for the parental BXPC3 cells. Consistent with this observation, increasing VDR levels in Panc1 cells (which has less VDR than BXPC3 cells) increased their $IC_{50}$ to gemcitabine by ~10-fold over controls.

The effects of VDR on gemcitabine sensitivity is ligand and dimerization dependent as VDR mutants lacking these activities failed to rescue the gemcitabine sensitivity of cells depleted of VDR. Furthermore, dominant negative mutants such as VDR S237M and the AML1/ETO oncogene fusion, both of which have been shown to sequester VDR from its partners such as RXR and Runx2, failed to rescue gemcitabine sensitivity. Despite the ligand dependence for gemcitabine survival, it is unclear if VD3 (1,25 dihydroxyvitamin D) is the ligand.

These studies were conducted using charcoal stripped and dialyzed serum that does not support VDR dependent transcription in the absence of an exogenous source of ligand. It is known that VDR can bind other ligands such as curcumin and lithocholic acid, the latter of which is a toxic bile acid that activates VDR-dependent transcription of the CYP3A detoxifying gene that is independent of VD3.

It was showed that VDR was essential for pancreatic cancer cells to form Rad51 and foci in response to gemcitabine. In BxPC3 cells that expressed the highest levels of VDR, Rad51 and phospho-γH2AX foci form 8 and 4 hours respectively, after addition of gemcitabine and the number and intensity of foci increase for up to 18 hours. In Panc1 cells which have lower VDR levels, or when VDR was experimentally depleted from BXPC3 cells, the kinetics of Rad51 and phospho-γH2AX foci formation was delayed by 4 and 6 hours respectively, and the intensity of the foci was reduced 1.5 and 2 fold respectively, and never reached the levels seen in control cells. Furthermore, the diffuse staining pattern of Rad51 and phospho-γH2AX that is seen in the nuclei of VDR depleted cells has been interpreted to reflect catastrophic amounts of DNA damage.

Without intending to be limited to any particular theory or mechanism of action, it is believed that VDR facilitates Rad51 dependent homologous recombination. Both BxPC3 and Panc1 cells were sensitized to the PARP inhibitor Rucaparib after VDR knockdown when compared to control cells. It was also observed that the levels of VDR negatively correlated with Rucaparib sensitivity as Panc1 cells (which has less VDR) were more sensitive to Rucaparib than BxPC3 cells. These data suggest that the level of VDR expression maybe a determinant of HR repair efficiency in PCa cells and, thus, maybe used as a predictive marker for PARP inhibitors.

The mechanism by which VDR facilitates Rad51 foci formation does not appear to be at the level of transcription. Cells depleted of VDR expressed Rad51 protein at levels comparable to control cells. This was corroborated by RNAseq data which showed no significant difference in mRNA levels of not only Rad51 but many of the proteins that are known to be important for Rad51 foci formation. The defect lies at the level of recruitment of Rad51 to sites of damage.

The defect may be at the level of histone acetylation which is known to be important for Rad51 formation. Indeed, Rad51 foci formation in VDR depleted cells can be rescued with an HDAC inhibitor (TSA). However, TSA did not increase gemcitabine resistance as it may exert other effects that are toxic to cells. Conversely, when the p300 HAT was depleted from VDR expressing cells, they failed to form Rad51 foci after gemcitabine treatment.

The invention is not limited to the embodiments described and exemplified above, but is capable of variation and modification within the scope of the appended claims.

We claim:

1. A method for killing tumor cells expressing the vitamin D receptor, comprising contacting the tumor cells with a therapeutically effective amount of a vitamin D receptor ligand selected from the group consisting of calcitriol, calcipotriol, eldecalcitol, lisinopril, elocalcitol, paricalcitol, seocalcitol, or any combination thereof, and contacting the tumor cells with a therapeutically effective amount of a Poly(ADP) Ribose Polymerase 1 (PARP-1) inhibitor selected from the group consisting of olaparib, iniparib, rucaparib, veliparib, MK 4827, BMN673, BSI 401, or any combination thereof, wherein the tumor cells are pancreatic tumor cells, breast tumor cells or ovarian tumor cells.

2. The method of claim 1, further comprising inducing double stranded DNA breaks in the chromosomal DNA of the tumor cells.

3. The method of claim 2, wherein inducing double stranded DNA breaks comprises irradiating the chromosomal DNA of the tumor cells.

4. The method of claim 2, wherein inducing double stranded DNA breaks comprises contacting the tumor cells with an amount of gemcitabine effective to induce double stranded DNA breaks.

5. The method of claim 1, wherein the tumor cells expressing the vitamin D receptor are resistant to the PARP-1 inhibitor.

6. The method of claim 1, wherein the PARP-1 inhibitor is selected from the group consisting of olaparib, rucaparib, and veliparib.

7. The method of claim 6, wherein the tumor cells expressing the vitamin D receptor are resistant to olaparib, rucaparib, or veliparib.

8. The method of claim 1, wherein the PARP-1 inhibitor is rucaparib.

9. The method of claim 8, wherein the vitamin D receptor ligand is selected from the group consisting of calcitriol, calcipotriol, eldecalcitol, and paricalcitol.

10. The method of claim 6, wherein the vitamin D receptor ligand is selected from the group consisting of calcitriol, calcipotriol, eldecalcitol, and paricalcitol.

11. The method of claim 9, further comprising inducing double stranded DNA breaks in the chromosomal DNA of the tumor cells.

12. The method of claim 11, wherein inducing double stranded DNA breaks comprises irradiating the chromosomal DNA of the tumor cells.

13. The method of claim 11, wherein inducing double stranded DNA breaks comprises contacting the tumor cells with an amount of gemcitabine effective to induce double stranded DNA breaks.

14. The method of claim 10, further comprising inducing double stranded DNA breaks in the chromosomal DNA of the tumor cells.

15. The method of claim 14, wherein inducing double stranded DNA breaks comprises irradiating the chromosomal DNA of the tumor cells.

16. The method of claim 14, wherein inducing double stranded DNA breaks comprises contacting the tumor cells with an amount of gemcitabine effective to induce double stranded DNA breaks.

17. The method of claim 8, wherein the vitamin D receptor ligand is paricalcitol.

18. The method of claim 17, further comprising inducing double stranded DNA breaks in the chromosomal DNA of the tumor cells.

19. The method of claim 18, wherein inducing double stranded DNA breaks comprises irradiating the chromosomal DNA of the tumor cells.

20. The method of claim 18, wherein inducing double stranded DNA breaks comprises contacting the tumor cells with an amount of gemcitabine effective to induce double stranded DNA breaks.

* * * * *